US008053182B2

(12) United States Patent
Cappola et al.

(10) Patent No.: US 8,053,182 B2
(45) Date of Patent: Nov. 8, 2011

(54) PREDICTORS OF TRANSPLANT REJECTION DETERMINED BY PERIPHERAL BLOOD GENE-EXPRESSION PROFILING

(75) Inventors: Thomas Cappola, Philadelphia, PA (US); Jonathan A. Epstein, Radnor, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1032 days.

(21) Appl. No.: 10/587,569

(22) PCT Filed: Jan. 31, 2005

(86) PCT No.: PCT/US2005/002697
§ 371 (c)(1),
(2), (4) Date: Jul. 31, 2006

(87) PCT Pub. No.: WO2005/074540
PCT Pub. Date: Aug. 18, 2005

(65) Prior Publication Data
US 2008/0274906 A1 Nov. 6, 2008

Related U.S. Application Data

(60) Provisional application No. 60/540,896, filed on Jan. 30, 2004.

(51) Int. Cl.
*C12Q 1/68* (2006.01)
*C12P 19/34* (2006.01)
*C07H 21/02* (2006.01)

(52) U.S. Cl. .......... 435/6; 435/91.2; 536/23.1; 536/24.3

(58) Field of Classification Search ........................ None
See application file for complete search history.

(56) References Cited

U.S. PATENT DOCUMENTS

2001/0051344 A1* 12/2001 Shalon et al. .................... 435/6
2004/0009479 A1   1/2004 Wohlgemuth et al.

FOREIGN PATENT DOCUMENTS

WO    WO 9915700        4/1999
WO    WO 01/81916    * 11/2001

OTHER PUBLICATIONS

Cheung V.G. et al. Nature Genetics (Mar. 2003), vol. 33, p. 422-425.*
Baan C.C. et al. Clin Exp. Immunol. (1994) vol. 97, p. 293-298.*
Hoshikawa Y. et al. Physiol. Genomics (2003) vol. 12, p. 209-219.*
Perren Cobb J. et al. Crit Care Med (2002) vol. 30, No. 12, p. 2711-2721.*
Juppner H. Bone (Aug. 1995) vol. 17, No. 2, Supplement, p. 39S-42S.*
Whitney A.R. et al. PNAS (Feb. 2003), vol. 100, No. 4, p. 1896-1901.*
Flechner S.M. et al. American Journal of Transplantation (2004) vol. 4, p. 1475-1489.*
Billingham ME. et al "A working formulation for the standardization of nomenclature in the diagnosis of heart and lung rejection: Heart Rejection Study Group". The International Society for Heart Transplantation. J Heart Transplant. 1990;9:587-93.
Pophal SG. et al "Complications of endomyocardial biopsy in children" J Am Coll Cardiol. 1999;34:2105-10.
de Groot-Kruseman HA et al, "Intragraft interleukin 2 mRNA expression during acute cellular rejection and left ventricular total wall thickness after heart transplantation". Heart. 2002;87:363-7.
Shulzhenko N. et al "Monitoring of intragraft and peripheral blood TIRC7 expression as a diagnostic tool for acute cardiac rejection in humans". Hum Immunol. 2001;62:342-7.
Shulzhenko N. et al "Intragraft activation of genes encoding cytotoxic T lymphocyte effector molecules precedes the histological evidence of rejection in human cardiac transplantation". Transplantation. 2001;72:1705-8.
Shulzhenko N, et al "Expression of CD40 ligand, interferon-gamma and Fas ligand genes in endomyocardial biopsies of human cardiac allografts: correlation with acute rejection". Braz J Med Biol Res. 2001;34:779-84.
van Emmerik N. et al "Cytokine gene expression profiles in human endomyocardial biopsy (EMB) derived lymphocyte cultures and in EMB tissue". Transpl Int. 1994;7 Suppl 1:S623-6.
Alpert S, Lewis NP et al "The relationship of granzyme A and perforin expression to cardiac allograft rejection and dysfunction". Transplantation. 1995;60:1478-85.
Baan CC et al "Cytokine mRNA expression in endomyocardial biopsies during acute rejection from human heart transplants". Clin Exp Immunol. 1994;97:293-8.
Kobashigawa JA. "Treatment of nonhemodynamic compromising rejection: conventional approaches vs individualization/new immunosuppressive drugs". Transplant Proc. 1997;29:37S-39S.
Li C, et al. "Model-based analysis of oligonucleotide arrays: expression index computation and outlier detection". 2001;98:31-36.
Seo J, et al. "Optimizing signal/noise ratios in expression profiling: project-specific algorithm selection and detection p value weighting in affymetrix microarrays". Bioinformatics. 2004.
Irizarry RA, et al "Speed TP. Exploration, Normalization, and Summaries of High Density Oligonucleotide Array Probe Level Data Biostatistics". 2003;4:249-264. Wu Z, et al "Preprocessing of oligonucleotide array data". Nat Biotechnol. 2004;22:656-8.
Ihake R et al "A Language for Data Analysis and Graphics. Journal of Graphical and Computational Statistics". 1996;5:299-314.
Tusher VG et al "Significance analysis of microarrays applied to the ionizing radiation response". Proc Natl Acad Sci U S A. 2001;98:5116-21.
Eisen MB et al "Cluster analysis and display of genome-wide expression patterns". 1998;95:14863-14868.
Kimball PM et al "The paradox of cytokine monitoring-predictor of immunologic activity as well as immunologic silence following cardiac transplantation". Transplantation. 1996;61:909-15.
Lagoo AS et al, "Semiquantitative measurement of cytokine messenger RNA in endomyocardium and peripheral blood mononuclear cells from human heart transplant recipients". Journal of Heart & Lung Transplantation. 1996;15:206-17.

(Continued)

*Primary Examiner* — Stephen Kapushoc
(74) *Attorney, Agent, or Firm* — Pearl Cohen Zedek Latzer, LLP; Mark S. Cohen

(57) ABSTRACT

The present invention provides methods and kits for predicting transplant rejection or tolerance. Methods for predicting the probability of cardiac allograft rejection via profiling of peripheral blood gene expression are also provided.

9 Claims, 6 Drawing Sheets

OTHER PUBLICATIONS

Morgun A et al "Cytokine and TIRC7 mRNA expression during acute rejection in cardiac allograft recipients". Transplant Proc. 2001;33:1610-1.

Valk PJ et al "Prognostically useful gene-expression profiles in acute myeloid leukemia". N Engl J Med. 2004;350:1617-28.

Bullinger L et al "Use of gene-expression profiling to identify prognostic subclasses in adult acute myeloid leukemia". N Engl J Med. 2004;350:1605-16.

Rosenwald A et al, "The use of molecular profiling to predict survival after chemotherapy for diffuse large-B-cell lymphoma". N Engl J Med. 2002;346:1937-47.

Sarwal M et al, "Molecular heterogeneity in acute renal allograft rejection identified by DNA microarray profiling". N Engl J Med. 2003;349:125-38.

Inohara N et al, "CLARP, a death effector domain-containing protein interacts with caspase-8 and regulates apoptosis". Proc Natl Acad Sci U S A. 1997;94:10717-22.

Expression profiling—best practices for data generation and interpretation in clinical trials. The Tumor Analysis Best Practices Working Group. Nat Rev Genet. 2004;5:229-37.

Baechler EC et al, "Expression levels for many genes in human peripheral blood cells are highly sensitive to ex vivo incubation". Genes Immun. 2004.

Guerette B et al "Increased granzyme B mRNA after alloincompatible myoblast transplantation" Transplantation, Williams and Wilkins, Baltimore, MD US., vol. 60, No. 9, Nov. 15, 1995 (pp. 1011-1016.

Tewari, M. et al "Lymphoid expression and regulation of A20, an inhibitor of programmed call death" J. Immunol., vo. 154, No. 4 1995, pp. 1699-1706.

Clement, M.V. et al "Perforin and granzyme B expression is associated with sever acute rejection" Transplantation, vol., 57 No. 3, 1994, pp. 322-326.

Strehlau J., et al "Quantificative detection of immune activation transcripts as a diagnostic tool in kidney transplantation" Proceedings of the National Academy of Sciences of USA, National Academy of Science, Washington, US, vol. 94, 1997, pp. 695-700.

Griffiths G M et al Granzyme A and perforin as markers for rejection in cardiac transplantation: European Journal of Immunology, Weinheim, de, vol. 21, 1991, pp. 687-692.

Lipman M.L. et al "Heightened intragraft cytotoxic T lypmphocyte gene expression in acutely rejecting renal allografts" J. Immunol., vol. 152, 1994, pp. 5120-5127.

Soares, M.P. et al "Expression of heme oxygenase-1 can determine cardiac xenograft survival" Mat. Med., vol. 4, No. 9, Sep. 1998, pp. 1073-1077.

* cited by examiner (1) Figure 1

SEQUENCE LISTING

<160> NUMBER OF SEQ ID NOS: 12

<210> SEQ ID NO 1
<211> LENGTH: 487
<212> TYPE: DNA
<213> ORGANISM: Human

<400> SEQUENCE: 1

```
aggtccctcc cacaacaatg ggaattatag gcaatataat tcaagatgag atttgggtgg      60
agacacggcc aaactgtatc acattgtatg tggatatgtt aatttttta aacatacaga     120 cataaaaatt gctagaaatt accgacaaga aaagcaaatt ttgaataaat tgaattctgg     180
aaatataaaa cgggcttgtt tttagaatac aaaatcagat gttaattcct gtgactgact     240
gaatatagaa aggtaaccta aggctgggca cggtggctcg tgcctatagt cctggcactt     300
tgagtggctg aggtgggtgg attgcttgaa accaggagtt cgagaccagc caaggcaaca     360
tggtgaaacc tcatccctac agaaaataca aaaatttgct gggtgtggtg gcacacacct     420
gtagtctcag ctactcggga ggctgaggtg ggaggattgc ttgagctcag gaggtcgagg     480
cttcagt                                                              487
```

<210> SEQ ID NO 2
<211> LENGTH: 432
<212> TYPE: DNA
<213> ORGANISM: Human

<400> SEQUENCE: 2

```
tcaaggggtt gctcagatgg gccgggcatg gtggctcacg cctgtaacct cagcactgtg      60
ggaggccaag ggggcagatc acttcaggtc gggagttcca gaccagcctg ttcaacatgg     120
cgaaacccca ttctaccaaa actacaaaaa ttagccgggc tcacgcctga aatcccagca     180
ctttgggaga ctgaggaggg gtcacctgag gtcaggatgt caagatcaga ctggccaaca     240
gaatgaaacc ctgtctctac aaaaatacaa aaattaggcc gggtgccgtg gctcatgcct     300
gtaatcccag cactttggga ggccgaggcg ggcagatcac aaggtcaggt gatcgagacc     360
atcctggcta acttggtgaa accctgtctc tactaaaaaa aaaatacaga aagttagccg     420
ggcgtggcac ct                                                         432
```

<210> SEQ ID NO 3
<211> LENGTH: 368
<212> TYPE: DNA
<213> ORGANISM: Human

<400> SEQUENCE: 3

```
gaagctttgg gcttcggtgg gtgcaggctc agcgatgaac atctggctgg ggcagctcct      60
```

```
ggggagcatc agggaagagg gggccatgag ccggccagca gtggagacgg cagtccagtt      120
tctctcccct ctgaccccta gaagggagt tgtagcccca tgaactagtt tcttgtctgg      180
gtcaggaaca agggccggct ggggcctggg gtgcagctgg tgtcagggta tgctgttttgc    240 tgatgggcag ggacacccct gcaggtctc gggctctgag cccaggacat tccctgcccc     300
ttgctcacct tggctgtggg ctgtgaacat tccgggaccc tgggcatctt atctaggtcc    360
gtgcagcc                                                             368

<210> SEQ ID NO 4
<211> LENGTH: 302
<212> TYPE: DNA
<213> ORGANISM: Human

<400> SEQUENCE: 4
aaagcttatc caccacgatt aagccggctt catccctggg atgcaaggct ggttcagcat    60
acacaaatga ataaacataa tccatcacac aaacagaacc aatgacaaaa gccacatgat    120
atttacctgt ataccttttt aagtacaaat aaatctgggc tgtcattatt tatgctaaca    180
ctggttttgt gtccctggaa tctatctatc taagtttttt tttctttttt tcttttccca   240
ttttccagta cctattagac agaatggctt tcaattttt ctcttacttc caaacttagt    300
ca                                                                    302

<210> SEQ ID NO 5
<211> LENGTH: 308
<212> TYPE: DNA
<213> ORGANISM: Human

<400> SEQUENCE: 5 gttattttc ttagtcctat gttctttatt ttggtgtttt ccattggata cctgcatgcc      60
aagtgttgtg ctacagtatt actgaagagt ataatggaag taatgtcctg ctgaaaattt   120
tctttgagat attaatcatt aataatttat atattgctat ttaatactta cataggtctt    180 tagccttta aaggatttct gtttgacagc ttttataatt gaaagttatt ccatttttt     240 tttaattttg catgcttgaa aaagatgaaa acagtgattt aaattatgaa gtatggggcc    300
aggtgcag                                                              308

<210> SEQ ID NO 6
<211> LENGTH: 556
<212> TYPE: DNA
<213> ORGANISM: Human

<400> SEQUENCE: 6
tagccgacca tggtggtgca tgcctgtagt cccagctatt cgggaggctg aggtaagagg     60
atcacctaag cctgtgaggt catggttgca atgagtcatg atcacgccac tgcgctacag   120
cctgggcgac acagtaagac cctgtctcaa aaaaagaag tgtgtttctg gccaggcacg    180
gtggctcacg cctgtaatcc cagcactttg ggaggcctag gtgggcagat catgaggtca    240
ggagttcgag accagcctgg ccaacatggc gaaacacctg tctctactaa aaatacaaaa   300
attaggccgg gcgcagtggc tcacacctgt aatcccaaca ctttgggagg ccgacccaga    360
tgggtggatc acctgaggtc aggagtttga ccagccctt gacaacatgg tgaaacccca     420
tctctggtag aaaatataaa aattaaccgg gcatggtggt ggacgcctgt aatcccagct    480
acttgggagg ctgaggcaga ataatcgctt gaacccagga ggcagaggtt gcagtaagcc    540
aagatcgtgc ctctgc                                                   556
```

<210> SEQ ID NO 7
<211> LENGTH: 302
<212> TYPE: DNA
<213> ORGANISM: Human

<400> SEQUENCE: 7

```
aaagcttatc caccacgatt aagccggctt catccctggg atgcaaggct ggttcagcat      60
acacaaatga ataaacataa tccatcacac aaacagaacc aatgacaaaa gccacatgat     120
atttacctgt atacctttt aagtacaaat aaatctgggc tgtcattatt tatgctaaca     180
ctggttttgt gtccctggaa tctatctatc taagttttt tttcttttt tcttttcca     240
ttttccagta cctattagac agaatggctt tcaattttt ctcttacttc caaacttagt     300
ca                                                                   302
```

<210> SEQ ID NO 8
<211> LENGTH: 444
<212> TYPE: DNA
<213> ORGANISM: Human

<400> SEQUENCE: 8

```
tagtcccagc cacacgggag gctgcggcag gaaaatggcg tgaacccggg aggcggagct      60
tgcagtgagc ggagatggcg ccactgcact ccaggctggg cgacagagcg agactccgtc    120
tcaaaaacaa accaacaaaa aaaaaacagg ccgggcgcgg tggctcatgc ctgtaaatcc    180
cagcactctg ggaggccgag gcgggcggat cacgaggtca ggagttcaag acagcctga    240
ccaacatggt gaaaccccgt ctcaactaaa aatacaaaaa ttagccgtgc gtggtggcac    300
gcacctgtaa tcccagctac tcaggaggcc gaggcaggag aatcgcccga acccgggagg    360
cagaggctgc agtgatccga gatcacgcca ctgcattcca gcctgggcga cagagcgaga    420
tttcatctcg ccgtgggcgg cgac                                          444
```

<210> SEQ ID NO 9
<211> LENGTH: 538
<212> TYPE: DNA
<213> ORGANISM: Human

<400> SEQUENCE: 9

```
ctgttgcaga gaggggtcct ggagaaatgg gttaccccag ttgtcttatt taaatggtta      60
cccatcagat tttaatttta tcttctcttt gagagcttgg taataagaag cacttaaatc    120
actccaaaga agactttaaa aagggagcag tgaaaaggtc ttaataattt attgattgaa    180
ttaagaaata ctagctaatt aagaatctga gtctaaacag cacagatttt ttctttctgc    240
ttttaaattg tgttttaaaa aaagagacag ggggctgggc gtggtggctc acgcctgtaa    300
tcctagcact ttgggaggcc gaggcgggtg gatcacgagg taggagttaa agaccagcct    360
ggccaacatg gcaaacccct actaaagata caaaaaaaa aaaaaattgg ccaggcgtgg    420
tggtgggtgc ctgtaatccc aggtacttgg aaggctgagg caggagaatc tcttgaaccc    480
agaaggcgaa ggttgcagtg aaccgagatc atgccattgt actctagcct gggtgaca     538
```

<210> SEQ ID NO 10
<211> LENGTH: 458
<212> TYPE: DNA
<213> ORGANISM: Human

<400> SEQUENCE: 10

```
atttcccatt ttcaaacctg acaagttggt cttgatgctg ttattcaaat aactgaaagt      60
```

-continued

```
aaatggttgt gaacaaggaa tttcagatca cagactcagt aagcctggcc agcccccaag      120
gctgtgtctt ccttaaagtt gggatctctg tattatctca tactctatag tagagcaata      180
aacataagct gacttatgtg atcacttaaa actaccagga agaaacattt tccgtaataa      240
atttagtgta ggattgcttt gtcttctcac actcactttt cagaaaagaa aatgtaagta      300
ttgccaggcg cggtggctca cacctgtaat cccagcactt tgggaggctg aggcaggtgg      360
atcacttgag gtcaggagtt ggagaccagc ctggccaaca tggagaaatc ccatctctac      420
taaaaataca aaaattagcc gggtgtagtg gcgcatgc                              458

<210> SEQ ID NO 11
<211> LENGTH: 221
<212> TYPE: DNA
<213> ORGANISM: Human
<220> FEATURE:
<221> NAME/KEY: misc_feature
<222> LOCATION: (155)..(155)
<223> OTHER INFORMATION: n is a, c, g, or t

<400> SEQUENCE: 11
gatagtccat aatctttttg ggtctcactt ctgcaaattg gagttcatac ttgcgctatc       60
ttttgttgaa gaaccctcaa gatagttgca aaaagtattt tgaaaagtat aaagtgatgg      120
gtttaatgta aatgttttat tcaatactac tatcntctag actaatttgg ttgtagttca      180
cattacagta gctgcttcgt aagtgatttt tgggctgggc g                          221

<210> SEQ ID NO 12
<211> LENGTH: 229
<212> TYPE: DNA
<213> ORGANISM: Human

<400> SEQUENCE: 12
taaatccaat tgctgttatc ttttgttttt catggaatat ctcgcatctc agaacacagt       60
ttgggaatca tattttattt agtgttttca gatgctatct attatatcta agatatttca      120
catttagcca ttcgttttat aaaaaactcc aggcaaactc agctggactt ttcttgcttt      180
aataacagct ttattgagat acaattcaca tatcacgaaa ttcttttta                  229
```

PREDICTORS OF TRANSPLANT REJECTION DETERMINED BY PERIPHERAL BLOOD GENE-EXPRESSION PROFILING

CROSS-REFERENCE TO RELATED APPLICATIONS

This application is a National Phase Application of PCT International Application No. PCT/US05/02697, International Filing Date 31 Jan., 2005, claiming priority of U.S. Provisional Patent Application, 60/540,896, filed 30 Jan., 2004, both which are herby incorpoarted herein by reference in their entirety.

FIELD OF INVENTION

This invention relates to a method of predicting the probability of transplant rejection, in particular, the probability of cardiac allograft rejection, using peripheral blood gene expression profiling.

BACKGROUND OF THE INVENTION

Organ transplantation is a viable therapy for improving the quality of life in people with end-stage organ failure. Progress has been made in using bone marrow, kidneys, hearts, and livers from unrelated individuals, though transplant rejection remains a persistent problem. Another limiting factor in clinical transplantation is the persistent shortage of organs. For example, of the 265,000 patients with end-stage kidney disease in the U.S., only 5-6% will receive a transplant. Hepatitis C virus-related liver diseases is another source of increasing demand for liver transplants, whose incidence is on the rise with predictions reaching increases of at least five-fold in the next decade.

Typically, organ donors are heart-beating cadaver donors (HBD), which unfortunately, represent a supply source remaining relatively constant for the past ten years.

Organ rejection is a product of the immune system of the recipient, which recognizes the transplant as foreign tissue and develops immune reactivity, culminating in rejection of the transplanted/grafted tissue. Attempts to tolerize recipients to transplant tissue have not met with much success to date.

Early detection of transplant rejection affords the possibility of aggressive immunosuppressive therapy for preventing transplant rejection. Methods for predicting transplant tolerance are clearly desirable for both diminishing potentially, the amount/duration of immunosuppressive therapy in successful recipients, and increasing the likelihood of successful transplantation in a particular recipient with respect to a given donor.

With the limited donor-pool, the criticality of donor choice and the clinical and economical consequences of transplant rejection, it is apparent, that new and inproved methods for predicting the probability of transplant rejection are greatly needed.

SUMMARY OF THE INVENTION

In one embodiment, the present invention provides a method for predicting transplant rejection in a subject, comprising determining a gene expression profile, wherein the gene expression profile comprises increased expression of at least 4 genes as compared to a standard, concurrent with diminished expression of at least one gene, as compared to the standard.

In another embodiment, the at least 4 genes with increased expression, are in combinations of four or more UQCRB, BTF3, ST13, CUL4A, TERF2IP, ARRB2, or NPEPPS genes.

In one embodiment, the gene with diminished expressionis an ARRB2, NPEPPS, PIGB, APC, BCL7A, EDG4, IL17R, PGF, NFAT5, BIRC1, LILRB3, TM6SF2, CFLAR, SOD2, SLC16A3 or SCD4 gene, or a combination thereof.

In another embodiment, the present invention provides a method for identifying a candidate for successful allograft transplantation comprising determining a gene expression profile, wherein the expression profile comprises increased expression of at least 1 gene as compared with a standard, concurrent with diminished expression of at least 4 genes compared with said standard.

In one embodiment, the invention provides a medium having disposed thereon an oligonucleotide-hybridized cRNA of UQCRB, BTF3, ST13, CUL4A, TERF2IP, ARRB2, NPEPPS, ARRB2, NPEPPS, PIGB, APC, BCL7A, EDG4, IL17R, PGF, NFAT5, BIRC1, LILRB3, TM6SF2, CFLAR, SOD2, SLC16A3 and SCD4.

In another embodiment, the invention provides a kit for predicting transplant tolerance, comprising a microarray comprising immobilized nucleic acids, wherein said nucleic acids exhibit complementarity to a UQCRB, BTF3, ST13, CUL4A, TER21P, ARRB2, NPEPPS, ARRB2, NPEPPS, PIGB, APC, BCL7A, EDG4, IL17R, PGF, NFAT5, BIRC1, LILRB3, TM6SF2, CFLAR, SOD2, SLC16A3, and SCD4 gene, or fragments thereof.

DETAILED DESCRIPTION OF THE INVENTION

Figure 1:
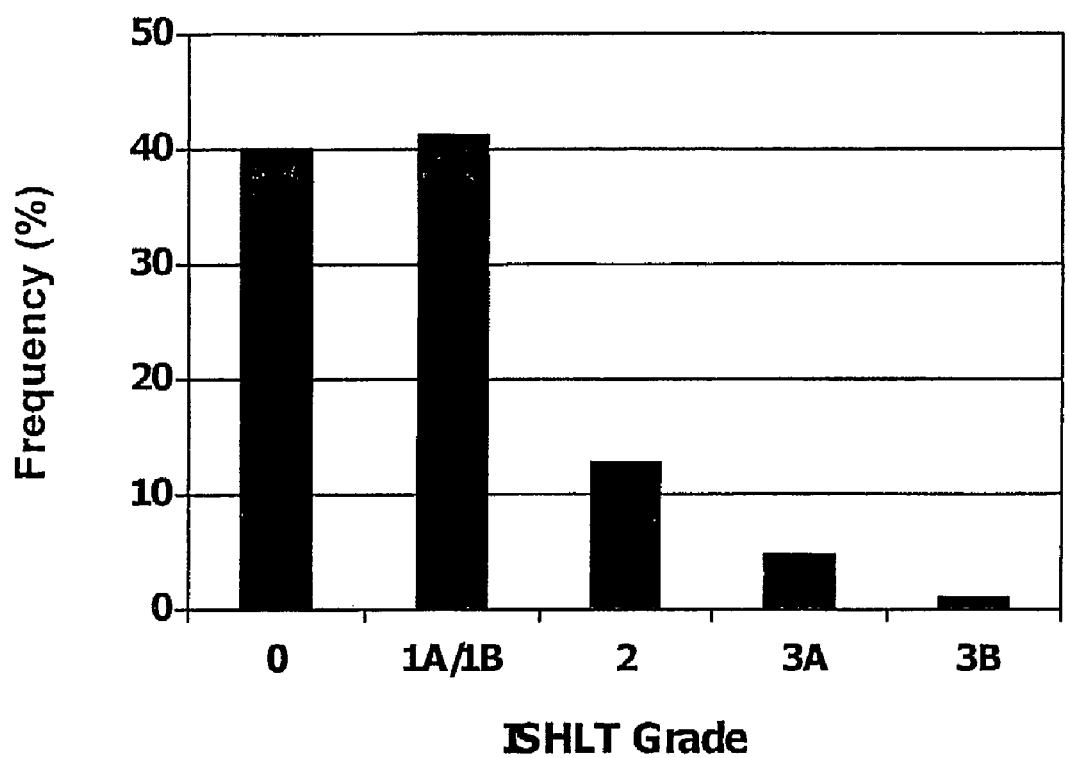
FIG. 1 is a graph showing distribution of rejection by ISHLT biopsy grade in the cohort of transplant recipients (189 transplant recipients; 409 biopsies).

Successful organ transplantation necessitates the prevention of organ rejection by the immune system. Organ transplants refers to any organ transplant from a donor to recipient, including allograft and xenograft transplantation.

In one embodiment, the present invention provides a method for predicting transplant rejection in a subject, comprising determining a gene expression profile, wherein the gene expression profile comprises increased expression of at least 4 genes as compared to a standard, concurrent with diminished expression of at least one gene, as compared to the standard.

In one embodiment graft rejection was associated with increased expression of UQCRB, BTF3, ST13, CUL4A, TERF2IP, ARRB2, or NPEPPS genes (Table II). In addition, graft rejection was also associated with diminished expression of ARRB2, NPEPPS, PIGB, APC, BCL7A, EDG4, IL17R, PGF, NFAT5, BIRC1, LILRB3, TM6SF2, CFLAR, SOD2, SLC16A3 and SCD4 (Table II).

In one embodiment, transplant rejection involves gross symptoms, which in another embodiment may be elevated temperature or significant failures of the function of the transplant. In another embodiment, transplant rejection involves T-cell activation, or in another embodiment clinical symptoms range from fever and malaise similar to an influenza-like syndrome, and in another embodiment to a fulminant and potentially fatal systemic illness. In one embodiment, transplant rejection involves glomerulopathy, or in another embodiment, transplant rejection involves fatigue, general weakness, tenderness or pain over transplant, light colored stool, increased blood pressure, dark colored urine, decreased urine output, jaundice, sudden weight gain, increased liver enzymes, increased BUN and creatinine, difficulty in breathing, post transplant proliferative disorders (PLTD's). In one embodiment, transplant rejection involves any one of infection, hypertension, diabetes, dyslipideinia, osteoporosis, graft coronary disease, renal insufficiency, malignancy, or their combination. It is to be understood that the methods of this invention may be employed in individuals prior to the onset or concurrent with evidence of any of these symptoms, as a means of predicting a likelihood for transplant rejection, in one embodiment, or in another embodiment, as an indicator for a need to provide greater immunosuppressive therapy, as described and exemplified herein.

The methods of this invention are also useful in predicting tolerance of a recipient to a transplant. In one embodiment, "tolerance", refers to a lack of evidence of an immune response at a transplant site in a recipient whose end result is to damage the transplanted tissue. In one embodiment, tolerance refers to the inhibition or prevention of a recipient's immune response against a donor graft, or in another embodiment, the reverse occurs, wherein graft versus host disease is prevented in the recipient. It is to be understood that any situation in a recipient wherein the transplanted tissue remains undamaged, or minimally damaged, in the recipient, over a course of time, is to be considered as part of this invention. In one embodiment, "tolerance", refers not only to complete immunologic tolerance to an antigen, but to partial immunologic tolerance, which, in one embodiment can be a degree of tolerance to an antigen which is greater than what would be seen if a method of the invention were not employed. In another embodiment, "tolerance", refers to a donor antigen-specific inhibition of the immune system as opposed to the broad-spectrum inhibition of the immune system seen with immunosuppressants. In one embodiment, "tolerance", refers to the ability of the graft to survive in an MHC mismatched or xenogeneic recipient without chronic immunosuppression, or in another embodiment, with minimal immunosuppression, or in another embodiment, with fewer drugs required for immunosuppression, or in another embodiment, with lower dosage of immunosuppression drugs, or in another embodiment, lower frequency of taking immunosuppression drugs, or in another embodiment, with fewer side effects associated with immunosuppression.

In one embodiment, treatment involves optimization of immunosuppressive therapy, or in another embodiment prevention of complications resulting from the transplant or the immunosuppressive agents, or in another embodiment, treatment of those complications when they arise. In one embodiment, immunosuppressive therapy consists of combination therapy with a calcineurin inhibitor which in another embodiment may be cyclosporine or tacrolimus, or in one embodiment combination therapy may further include corticosteroids, and an antimetabolite agent which in another embodiment may be, azathioprine or mycophenolate mofetil. In one embodiment, the corticosteroid is weaned and discontinued 1 to 2 years following transplantation and in another embodiment, the patient is managed chronically with a two-drug immunosuppressive regimen. The methods of this invention, in one embodiment, serve to predict the magnitude or duration, etc., of drug therapy necessary to maintain transplant tolerance.

In one embodiment, the present invention provides a method for predicting transplant rejection in a subject, comprising determining a gene expression profile.

In one embodiment, the term "determining" refers to techniques to analyze the level of expression of specific genes in cells and tissues. These techniques include in one embodiment, Northern blot analysis, RNAse protection assays, PCR, including quantitative PCR, as will be known to one skilled in the art. In one embodiment, microarray technology is used to determine gene expression profiles, as will be understood by one skilled in the art, and as exemplified hereinbelow In one embodiment, the term "gene" refers to a nucleic acid fragments that encode proteins including regulatory sequences preceding (5' non-coding sequences) and following (3' non-coding sequences) the coding sequence. In one embodiment, "coding sequence" refers to a nucleotide sequence that codes for a specific amino acid sequence. In another embodiment, "regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. In one embodiment, regulatory sequences may include promoters, translation leader sequences, introns, and polyadenylation recognition sequences.

A "nucleic acid" refers in one embodiment to the phosphate ester polymeric form of ribonucleosides (adenosine, guanosine, uridine or cytidine; "RNA molecules") or in another embodiment, to deoxyribonucleosides (deoxyadenosine, deoxyguanosine, deoxythyinidine, or deoxycytidine; "DNA molecules"). In one embodiment "nucleic acid" refers to a single stranded form, or in another embodiment, a double-stranded helix. In one embodiment, double stranded DNA-DNA or, in another embodiment DNA-RNA or, in another embodiment RNA-RNA helices are possible. The term nucleic acid molecule, and in particular DNA or RNA molecule, refers in one embodiment only to the primary and secondary structure of the molecule, and does not limit it to any particular tertiary forms.

In another embodiment, the term "expression" refers to the transcription and stable accumulation of sense (mRNA) or antisense RNA derived from the nucleic acid fragment or fragments of the invention. Expression may refer in one embodiment, to translation of mRNA into a polypeptide.

In one embodiment, the term "expression profile" refers to the results obtained upon differentially determining expression of at least 5 genes or their products, when compared to a standard. The profile is assigned to a given subject, which reflects comparative results between his or her expression of the at least 5 genes or their products as compared to a standard. In one embodiment, the expression profile further comprises a determination of relative expression of nucleic acids, which do not code for a functional protein, as compared to the standard.

The term "differentially expressed" refers to a relative abundance or absence of expression in a subject as compared to a standard. Differential expression refers to changed expression, either higher or lower, in the subject, as compared to the standard.

Differential gene expression may include in one embodiment, a comparison of expression between two or more genes, or in another embodiment, a comparison of the ratios of the expression between two or more genes, or in another embodiment, a comparison of two differently processed products of the same gene, which differ between control subjects and subjects in which transplant was rejected, or in another embodiment, in the same subject pre- and post transplantation. Differential expression refers in one embodiment to quantitative, as well as in another embodiment, qualitative, differences in the temporal or cellular expression pattern in a gene or its expression products as described herein.

In one embodiment, a gene expression profile is compiled using a sample of peripheral blood of a subject being evaluated. In another embodiment, a tissue biopsy serves as the source for evaluation, or in another embodiment, the end-stage diseased organ, whose replacement is desired is used as the source for gene expression profile.

The gene expression profile compiled in the methods of this invention will comprise genes differentially expressed in successful transplant recipients, as compared to those prone to transplant rejection. The pattern of the differentially expressed genes will comprise increased expression of at least 4 genes simultaneous with diminished expression of at least 1 gene, in subjects more likely to reject a transplant, whereas the reverse profile is more predictive of success of a transplant in a given subject.

In one embodiment, determining the gene expression profile refers to methods to assess mRNA abundance, or in another embodiment, gene product abundance. According to this aspect of the invention, and in one embodiment, gene product refers to the translated protein. In one embodiment, protein abundance reflects gene expression profiles, which may be determined, in other embodiments, by any methods known in the art, such as, but not limited to Western blot analysis, RIA, ELISA, HPLC, functional assays, such as enzymatic assays, as applicable, and others. In one embodiment, expression profile is determined by a change in mRNA levels, or in another embodiment in surface expression, or in another embodiment in secretion or in another embodiment other partitioning of a polypeptide.

In another embodiment, the expression profile is a relative value as compared to a standard. In one embodiment the term "standard" may refer to a pooled sample of successful recipients for the same organ transplant. In another embodiment, standard may be ethnically- or gender- or age-matched recipients. It is to be understood that the standard may be derived from any subject, or pool of subjects, whose expression profile or profiles, once generated, is sufficient to detect even minute relative differences in expression, when compared to a potential transplant recipient, or in another embodiment, transplant recipient.

In one embodiment, "increased expression" refers to an increase in the level or in another embodiment, activity of target gene product relative to the level or activity of target gene product in a standard. In another embodiment, increased expression refers to between a 10 to about a 250% increase in mRNA levels, or in another embodiment, in protein levels. In another embodiment, increased expression refers to changes in gene expression at the mRNA or protein level, in terms of its pattern of expression in particular examples, such as, for example, and in one embodiment, increased expression in tissue, but not in the blood, for example, in damaged tissue for which the transplant is required. In one embodiment, increased expression is synonymous with overexpression, or stimulated expression. In another embodiment, increased expression is a relative determination, wherein expression is greater than the standard, or in cases where expression is absent in the standard, this despite expression being barely detectable in the subject. It is to be understood that any such circumstance described hereinabove, represents increased expression for the methods of this invention.

In one embodiment, "diminished expression" refers to a reduction in the level or in another embodiment, activity of target gene product relative to the level or activity of the target gene product in a standard. In one embodiment, diminished expression is synonymous with decreased expression, or in another embodiment with underexpression. In one embodiment, the expression of the gene or product is absent in the subject, or slightly less than the standard. In one embodiment, the expression of the gene is diminished by at least 25% (for example, as depicted in FIG. 2B).

In one embodiment, "compared to a standard", refers to relative changes in expression where the standard is derived from a single individual, or is derived from pooled subjects who have successfully undergone a transplant. In another embodiment, a standard can be derived from a single subject following about 1 to about 5 years of having undergone successful transplantion. In one embodiment, a standard can be derived from a subject who has undergone transplant of the specific tissue for which the subject is being evaluated, such as, for example, being obtained from a subject having undergone a successful cardiac transplant. In another embodiment, the standard is derived from a subject who has undergone transplant of a different tissue type than that sought by the recipient, however, the two individuals, or pool of individuals are of a similar genetic background.

In one embodiment, increases or decreases in gene expression are tissue specific, and encompass, in other embodiments, post-transcriptional and/or post-translational modifications of the gene products, which result in differences in non-modified gene expression.

Figures 2, 2A, 2B:
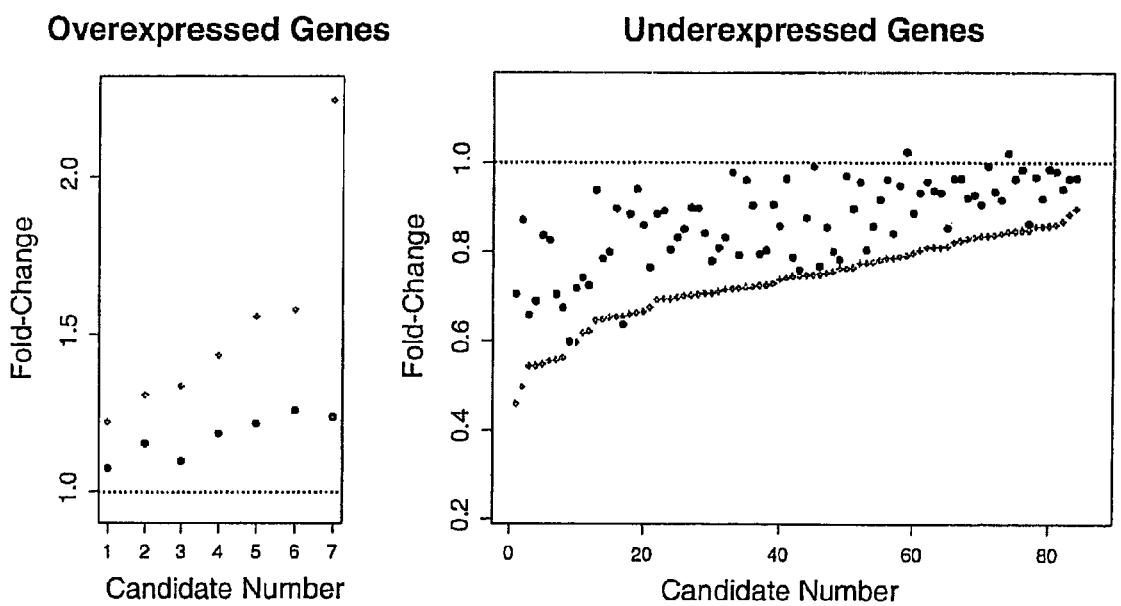
FIG. 2A is a graph showing differential gene expression in peripheral blood specimens from patients with biopsy-proven transplant rejection (n=7) and standards without rejection (n=7) for genes with increased expression.
FIG. 2B is a graph showing differential gene expression in peripheral blood specimens from patients with biopsy-proven transplant rejection (n=7) and standards without rejection (n=7) for genes with diminished expression.
Figure 3:
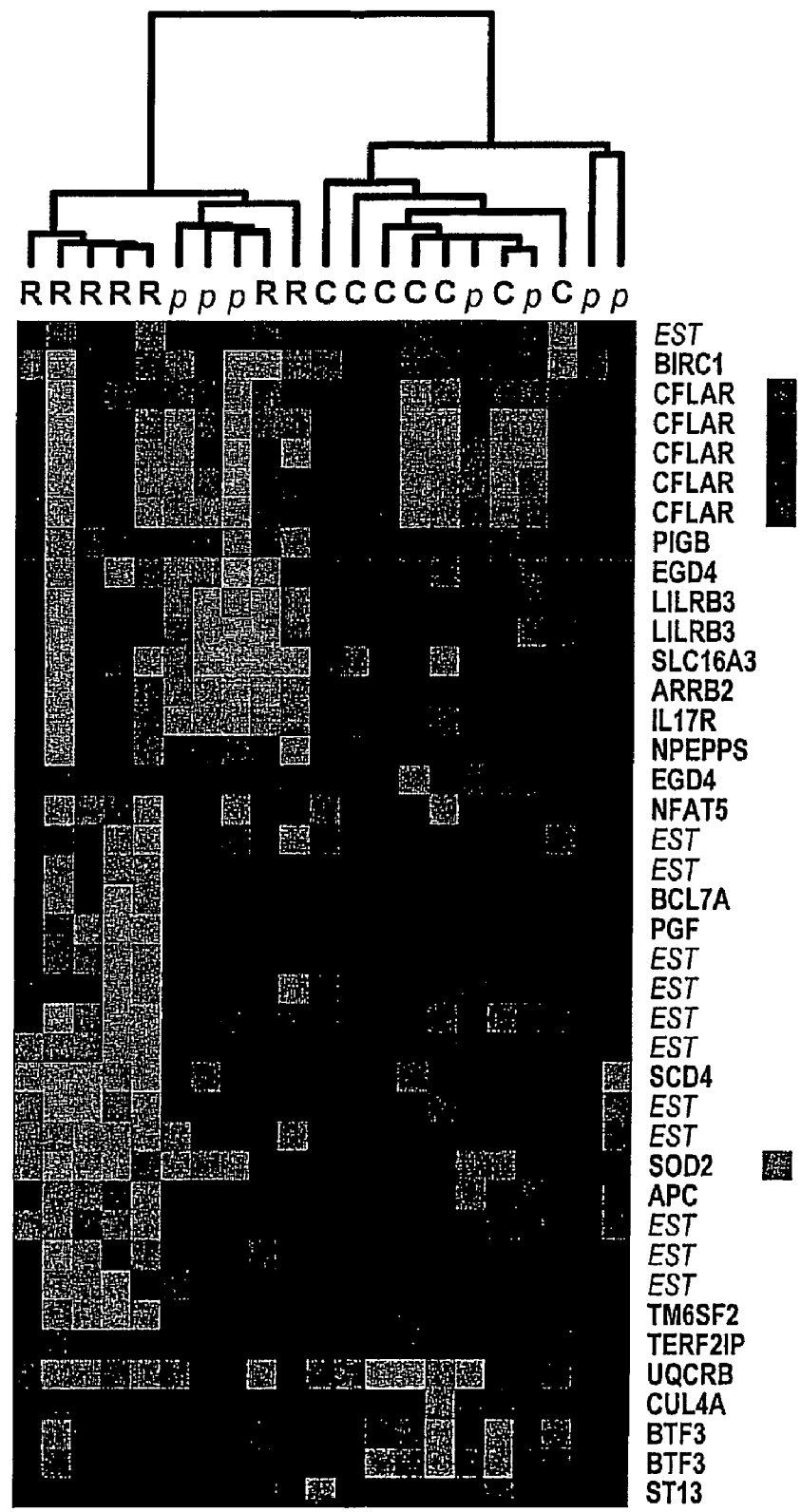
FIG. 3 is a graph showing cluster analysis of 40 candidate markers with hierarchical clustering (see Table 2 for full names and functional annotation of the 40 candidates).

In another embodiment UQCRB, BTF3, ST13, CUL4A, TERF2IP, ARRB2, and NPEPPS show increased expression (See FIGS. 2A, 3 and Example 1). In one embodiment, the genes showing increased expression in subjects, which in another embodiment are predicted to reject, or in another embodiment show no change or in another embodiment diminished expression in subjects which in another embodiment, will be tolerant to a transplant. In one embodiment, expression is a relative measure, when in comparison to a standard, as described hereinabove.

In one embodiment, genes whose expression is increased in potential transplant recipient, as compared to a standard, will encode a protein, whose amino acid sequence is homologous to those disclosed in NCBI's Entrez protein database, as illustrated in Table III.

In one embodiment, the term "homology" or "homologous" refers to a protein from another organism when the encoded amino acid sequence of the protein has a similar sequence to the encoded amino acid sequence of a protein from a different organism and in another embodiment, has a similar biological activity or in another embodiment, similar function. In one embodiment, a protein may have homology or be homologous to another protein if the two proteins have similar amino acid sequences and have similar biological activities or functions. In another embodiment, "homologous" does not necessarily imply that there is an evolutionary relationship between the proteins. In one embodiment, the term "homologous" refers to that the two proteins have similar amino acid sequences and similar biological activities or functions. In one embodiment, a homologous protein exhibits 50% sequence similarity to the wild type protein, or in another embodiment 60% sequence similarity, or in another embodiment 70% sequence similarity. or in another embodiment 80%, 85% or 90% sequence similarity to the wild type protein. or in another embodiment, a homologous protein exhibits 95%, 97%, 98% or 99% sequence similarity.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. A preferred algorithm when comparing a sequence of the invention to a database containing a large number of sequences from different organisms is the computer program BLAST, especially blastp or tblastn. The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

TABLE III

Genes which are overexpressed in subjects rejecting a transplant

| Gene | Unigen ID. | Accession No. |
|---|---|---|
| UQCRB | Hs.131255 | P14927 |
| BTF3 | Hs.529798 | JC1235, |
| ST13* | Hs.511834 | P50502, |
| CUL4A | Hs.339735 | NP_003580 |
| TERF2IP | Hs.301419 | NP_061848.1 |

In another embodiment the at least 4, overexpressed genes, are in combinations of four or more of UQCRB, BTF3, ST13, CUL4A, TERF2IP, ARRB2, or NPEPPS.

In one embodiment, the genes showing increased expression are increased by at least 30% as compared to a standard. In one embodiment, increased expression is by 30-100% of the standard, or between 100 and 150% of the standard, or between about 150 to about 200% of the standard, or between about 200 to about 250% of the standard. In one embodiment, the genes' expression are increased at least 30% or in another embodiment, the genes' expression are increased over 100%, or in another embodiment the genes' expression are increased over 150%, or in another embodiment the genes' expression are increased over 200%, or in another embodiment the genes' expression are increased over 250%. Each of at least 4 genes evaluated in the profile will be expressed at greater levels as compared to the standard. In one embodiment, increased expression is an average finding, such that minute levels of increased expression of one gene and robust increased expression of another is sufficient to be predictive according to the methods of this invention.

In another embodiment ARRB2, NPEPPS, PIGB, APC, BCL7A, EDG4, IL17R, PGF, NFAT5, BIRC1, LILRB3, TM6SF2, CFLAR, SOD2, SLC16A3 and SCD4 show diminished expression (See FIGS. 2B, 3 and Example 1). In one embodiment, the genes showing diminished expression in subjects, which in another embodiment are predicted to reject, or in another embodiment show no change or in another embodiment increased expression in subjects which in another embodiment, will be tolerant to a transplant. In one embodiment, expression is a relative measure, when in comparison to a standard, as described hereinabove.

In one embodiment, genes whose expression is diminished in potential transplant recipient, as compared to a standard, will encode a protein, whose amino acid sequence is homologous to those disclosed in NCBI's Entrez protein database, as illustrated in Table IV

TABLE IV

Genes which are underexpressed in subjects rejecting a transplant

| Gene | Unigen ID. | Accession No. |
|---|---|---|
| ARRB2 | Hs.435811 | NP_004304.1 |
| NPEPPS | Hs.443837 | P55786 |
| PIGB | Hs.126115 | S71751, |
| APC | Hs.158932 | P25054 |
| BCL7A | Hs.530970 | NP_066273.1 |
| EDG4 | Hs.122575 | NP_004711.2 |
| IL17R | Hs.129751 | NP_060312.1 |
| PGF | Hs.252820 | A41236 |
| NFAT5 | Hs.371987 | NP_006590.1 |
| BIRC1 | Hs.519374 | Q13075 |
| LILRB3 | Hs.306230 | NP_006831.1 |
| TM6SF2* | Hs.531624 | NP_075379.1 |
| CFLAR | Hs.390736 | O15519 |
| SOD2 | Hs.487046 | NP_000627 |
| SLC16A3 | Hs.500761 | NP_004198.1 |
| SCD4 | Hs.379191 | NP_079182.1 |

In one embodiment, the genes showing diminished expression are diminished by at least 25% as compared to a standard. In one embodiment, diminished expression is by 25-30% of the standard, or between 30 and 35% of the standard, or between about 35 to about 40% of the standard, or between about 40 to about 75% of the standard. In one embodiment, the genes' expression are diminished at least 15% or in another embodiment, the genes' expression are diminished over 25%, or in another embodiment the genes' expression are diminished over 40%, or in another embodiment the genes' expression are diminished over 50. Each of the genes evaluated in the profile will be expressed at lower levels as compared to the standard. In one embodiment, diminished expression is an average finding, such that minute levels of diminished expression of one gene and virtual elimination in expression of another is sufficient to be predictive according to the methods of this invention.

In one embodiment, gene profile determination may be done in duplicate or in another embodiment in triplicate. In one embodiment, gene profile determination may be accomplished a year prior to a planned transplantation and, in another embodiment, repeat determinations may be conducted with regular frequency up to the time of transplantation. In another embodiment, gene profile determination may be conducted post-transplantation, and, in another embodiment, as a regular post-operative procedure. In another embodiment, post-transplant determinations may be used as an indicator for a need to increase, or in another embodiment, decrease, or in another embodiment, otherwise adjust immunosuppressive therapy.

In another embodiment, a gene showing diminished expression, does not encode for a known protein. In one embodiment, the gene showing diminished expression is an expressed sequence tag. As yet, many of the sequences identified in the human genome sequence are not annotated. The gene expression profile of the present invention, although not exhaustive, contemplates full analysis of any untranslated sequence. In one embodiment of the invention the method evaluates multiple genes simultaneously, wherein minute differences in expression may still be correlated with rejection or tolerance, as indicated herein.

In one embodiment the expressed sequence tag is a selected nucleic acid with a specified nucleic acid sequence. In another embodiment, a nucleic acid "probe" hybridizes to a nucleic acid "tag." In one embodiment, nucleic acid tags are incorporated as labels into biological libraries, and the tag nucleic acids are detected using an array of probes. In one embodiment a "list of tag nucleic acids" refers to a pool of tag nucleic acids, or a representation, which in one embodiment is an electronic or in another embodiment paper copy of the sequences in the pool of tag nucleic acids. In one embodiment, the pool of tags can be all possible tags of a specified length (i.e., all 20-mers), or, in another embodiment a subset thereof.

In one embodiment, a set of nucleic acid tags binds to a probe with minimal cross hybridization when a single species (or "type") of tag in the tag set accounts for the majority of all tags which bind to an array comprising a probe species.

In another embodiment, the expressed sequence tags described hereinabove have a nucleic. acid sequence as set forth in NCBI's Entrez nucleic acid database, having the SEQ ID Numbers from 1 to 12 as shown in Table IV hereinbelow

TABLE IV

Sequence ID No.'s for Expressed sequence tags and their sequence

| EST | Probe Set ID. | Unigen ID. | Target Sequence | SEQ ID NO. |
|---|---|---|---|---|
| 1. | 207365_x_at | Hs.468663 | aggtccctcccacaacaatgggaattataggcaatataattcaag atgagatttgggtggagacacggccaaactgtatcacattgtatgt ggatatgttaatttttttaaacatacagacataaaaattgctagaaatt accgacaagaaaagcaaattttgaataaaattgaattctggaaatat aaaacgggcttgttttagaatacaaaatcagatgttaattcctgtga ctgactgaatatagaaaggtaacctaaggctgggcacggtggct cgtgcctatagtcctggcactttgagtggctgaggtgggtggattg cttgaaaccaggagttcgagaccagccaaggcaacatggtgaa acctcatccctacagaaaatacaaaaatttgctgggtgtggtggca cacacctgtagtctcagctactcgggaggctgaggtgggaggat ggtcgaggcttcagt | 1 |
| 2. | 207730_x_at | Hs.43071 | tcaaggggttgctcagatgggccgggcatggtggctcacgcctg taacctcagcactgtgggaggccaaggggcagatcacttcag gtcgggagttccagaccagcctgttcaacatggcgaaacccatt ctaccaaaactacaaaaattagccgggctcacgcctgaaatccca gcactttgggagactgaggaggggtcacctgaggtcaggatgtc aagatcagactggccaacagaatgaaaccctgtctctaceaaaat acaaaaattaggccgggtgccgtggctcatgcctgtaatcccagc actttgggaggccgaggcgggcagatcacaaggtcaggtgatc gagaccatcctggctaacttggtgaaaccctgtctctactaaaaaa aaaatacagaaagttagccgggcgtggcacct | 2 |
| 3. | 205781_at | Hs.164410 | gaagctttgggcttcggtgggtgcaggctcagcgatgaacatctg gctggggcagctcctggggagcatcagggaagaggggggccat gagccggccagcagtggagacggcagtccagtttctctcccctc tgaccctagaaggggagttgtagccccatgaactagtttcttgtc tgggtcaggaacaagggccggctgggcctggggtgcagctg gtgtcagggtatgctgtttgctgatgggcagggacacccctgcag ggtctcgggctctgagcccaggacattccctgcccttgctcacc ttggctgtgggctgtgaacattccgggaccctgggcatcttatcta ggtccgtgcagcc | 3 |
| 4. | 220712_at | Hs.18166 | aaagcttatccaccacgattaagccggcttcatccctgggatgca aggctggttcagcatacacaaatgaataaacataatccatccacac aaacagaaccaatgacaaaagccacatgatatttacctgtatacct ttttaagtacaaataaatctgggctgtcattatttatgctaacactggt tttgtgtccctggaatctatctatctaagttttttttcttttttttcttttttcc atttccagtacctattagacagaatggctttcaattttttctcttacttc caaacttagtca | 4 |
| 5. | 215558_at | Hs.529925 | gttattttcttagtcctatgttctttattttggtgttttccattggatacct gcatgccaagtgttgtgctacagtattactgaagagtataattggaa gtaatgtcctgctgaaaatttctttgagatattaatcattaataatttat atattgctatttaatacttacataggtctttagccttttaaaggatttct gtttgacagcttttataattgaaagttattccatttttttttaatttttgcat gcttgaaaaagatgaaaacagtgatttaaattatgaagtatgggc caggtgcag | 5 |
| 6. | 220071_x_at | Hs.14347 | tagccgaccatggtggtgcatgcctgtagtcccagctattcggga ggctgaggtaagaggatcacctaagcctgtgaggtcatggttgc aatgagtcatgatcacgccactgcgctacagcctgggcgacaca gtaagaccctgtctcaaaaaaagaagtgtgtttctggccaggca cggtggctcacgcctgtaatcccagcactttgggaggcctaggtg ggcagatcatgaggtcaggagttcgagaccagcctggccaacat ggcgaaacctgtctctactaaaaatacaaaaattaggccgggc gcagtggctcacacctgtaatcccaacactttgggaggccgacc | 6 |

TABLE IV-continued

Sequence ID No.'s for Expressed sequence tags and their sequence

| EST | Probe Set ID. | Unigen ID. | Target Sequence | SEQ ID NO. |
|---|---|---|---|---|
| | | | cagatgggtggatcacctgaggtcaggagtttgagaccagcctt gacaacatggtgaaacccatctctggtagaaatataaaaaattaa ccgggcatggtggtggacgcctgtaatcccagctacttgggagg ctgaggcagaataatcgcttgaacccaggaggcagaggttgca gtaagccaagatcgtgcctctgc | |
| 7. | 221205_at | Hs.428360 | aaagcttatccaccacgattaagccggcttcatccctgggatgca aggctggttcagcatacacaaatgaataaacataatccatcacac aaacagaaccaatgacaaaagccacatgatatttacctgtatacct ttttaagtacaaataaatctgggctgtcattatttatgctaacactggt tttgtgtccctggaatctatctatctaagtttttttttcttttttctttttcc attttccagtacctattagacagaatggctttcaattttttctcttacttc caaacttagtca | 7 |
| 8. | 215978_x_at | Hs.288771 | tagtcccagccacacgggaggctgcggcaggaaaatggcgtga acccgggaggcggagcttgcagtgagcggagatggcgccact gcactccaggctgggcgacagagcgagactccgtctcaaaaac aaaccaacaaaaaaaaaacaggccgggcgcggtggctcatgc ctgtaaatcccagcactctgggaggccgaggcgggcggatcac gaggtcaggagttcaagaacagcctgaccaacatggtgaaacc ccgtctcaactaaaaatacaaaaattagccgtggtggtggcacg cacctgtaatcccagctactcaggaggccgaggcaggagaatc gcccgaacccgggaggcagaggctgcagtgatccgagatcac gccactgcattccagcctgggcgacagagcgagatttcatctcgc cgtgggcggcgac | 8 |
| 9. | 209703_x_at | Hs.471778 | ctgttgcagagaggggtcctggagaaatgggttaccccagttgtc ttatttaaatggttacccatcagattttaattttatcttctctttgagagc ttggtaataagaagcacttaaatcactccaaagaagactttaaaaa gggagcagtgaaaaggtcttaataatttattgattgaattaagaaat actagctaattaagaatctgagtctaaacagcacagattttttctttct gcttttaaattgtgttttaaaaaaagagacaggggctgggcgtgg tggctcacgcctgtaatcctagcactttgggaggccgaggcggg tggatcacgaggtaggagttaaagaccagcctggccaacatggc aaaaccctactaaagatacaaaaaaaaaaaaaaattggccaggc gtggtggtgggtgcctgtaatcccaggtacttggaaggctgagg caggagaatctcttgaacccagaaggcgaaggttgcagtgaacc gagatcatccattactctagcctggtaca | 9 |
| 10. | 215375_x_at | Hs.293563 | atttcccattttcaaacctgacaagttggtcttgatgctgttattcaaa taactaaagtaaatggttgtgaacaaggaatttcagatccagaag tcagtaagcctggccagcccccaaggctgtgtcttccttaaagttg ggatctctgtattatctcatactctatagtagagcaataaacataag ctgacttatgtgatcacttaaaactaccaggaagaaacattttccgt aataaatttagtgtaggattgcttttgtcttctcacactcacttttccaga aaagaaatgtaagtattgccaggcgcggtggctcacacctgtaa tcccagcactttgggaggctgaggcaggtggatcacttgaggtc aggagttggagaccagcctggccaacatggagaaatcccatctc tactaaaaatacaaaaattagccgggtgtagtggcgcatgc | 10 |
| 11. | 215029_at | Hs.306803 | gatagtccataatctttttgggtctcacttctgcaaattggagttcata cttgcgctatcttttgttgaagaaccctcaagatagttgcaaaaagt attttgaaaagtataaagtgatgggtttaatgtaaatgttttattcaat actactatcntctagactaatttggttgtagttcacattacagtagct gcttcgtaagtgattttttgggctgggcg | 11 |
| 12. | 216109_x_at | Hs.159799 | taaatccaattgctgttatcttttgtttttcatggaatatctcgcatctca gaacacagtttgggaatcatattttatttagtgttttcagatgctatct attatatctaagatatttcacatttagccattcgttttataaaaaactcc aggcaaactcagctggacttttcttgctttaataacagctttattgag atacaattcacatatcacgaaattcttttta | 12 |

In one embodiment, expression levels are determined prior to transplantation. In another embodiment, gene expression profiles are obtained after transplantation, and serve as an indicator for magnitude, or in another embodiment duration or in another embodiment dosage, or in another embodiment type of immunosuppressive therapy employed.

In one embodiment, when the subject appears to be a good candidate for transplant tolerance, the transplant donor may share fewer alleles of the MHC locus with the recipient, or in another embodiment, the minor histocompatibility factors.

The success of a transplant of an allograft in a host depends in one embodiment on factors such as the antigens on the transplanted tissue that are recognized by the recipient as foreign and in another embodiment, can evoke the rejection response, or in one embodiment the cells in the recipient's immune system that mediate rejection, and in another embodiment, the reactions that modify either the presentation of the foreign antigen or in one embodiment, the cellular response.

In one embodiment, the products of the major histocompatibility complex (MHC) play an important role in mediating an attack by the graft tissue against the recipient. The MHC in another embodiment, generally includes many different loci, each encoding separate cell-surface antigens, and in one embodiment, the loci has extensive polymoiphism. The loci of the MHC fall into one of two classes, Class II, based on their tissue distribution, the structure of the expressed antigens, and their functions.

In another embodiment, the term "histocompatibility" refers to the similarity of tissue between different individuals. The level of histocompatibility describes in one embodiment how well matched the patient and donor are. The major histocoinpatibility determinants are the human leukocyte antigens (HLA). HLA typing is performed between the potential donor and the potential transplant recipient to determine how close a HLA match the two are. The closer the match the less the donated tissue and the patient's body will react against each other.

In one embodiment, standard subject may be one who closely matches the transplant recipient based on HLA and MHC typing. In another embodiment, the standard subject may be a normal subject of the same age, or in another embodiment gender, or in another embodiment race, or in another embodiment immediate family member, all of which may in one embodiment be candidates for being donors, or in another embodiment after a successful transplant procedure, or in another embodiment following a transplant rejection.

In one embodiment, "match" refers to how similar the HLA and MHC typing is between the donor and the recipient. The best kind of match is an "identical match". This means that in one embodiment, all six of the HLA antigens (2 A antigens, 2 B antigens and 2 DR antigens) are the same between the donor and the recipient. This type of match is described as a "6 of 6" match. Donors and recipients who are "mismatched" at one antigen are considered a "5 of 6" match, and so forth. In one embodiment, the recipient may be determined to be a good candidate for transplant of an organ from a particular donor, despite the donor and recipient not having a 6 of 6 match. In one embodiment, the method is predictive of transplant tolerance in cases where the donor is a 5 of 6, or in another embodiment, 4 of 6, or in another embodiment, 3 of 6 match, with respect to the recipient.

In one embodiment, the method for determining the gene expression profile uses DNA microarray technology, as is known in the art, and in one embodiment, is exemplified hereinbelow. In another embodiment, nucleotide sequences of interest are plated, or arrayed, on a microchip substrate. The arrayed sequences are hybridized in another embodiment with specific DNA probes from cells or tissues of interest.

In another embodiment, the identified genes and/or gene products and/or modulators can be used to identify cells exhibiting or in another embodiment, predisposed to an immune response involving a transplant phenotype, thereby diagnosing subjects having, or at risk for developing, such response. In one embodiment, the identified genes and/or gene products can be used to determine severity or in another embodiment duration of such response.

In one embodiment, the transplant constitutes a heart, liver, kidney, bone, bone marrow, cornea, hair follicles and skin. In one embodiment, the transplant is cardiac. In another embodiment, the transplant is an allograft.

In one embodiment, the term allograft refers to grafts between two or more individuals allogeneic at one or more loci (usually with which is in one embodiment a histocompatibility loci. In another embodiment Allogeneic refers to when the genes at one or more loci are not identical in sequence in each organism. In one embodiment, the term "loci" refers to the site in a linkage map or on a chromosome where the gene for a particular trait is located. Any one of the alleles of a gene may be present at this site. Histocompatibility refers in one embodiment to a set of plasmalemmal glycoprotein antigens involved in rapid graft rejection and other immune phenomena. The minor histocompatibility (MHC) antigens are involved in much slower rejection phenomena. The major antigens show remarkable polymorphism and occur as Class I and Class II types.

In one embodiment, the term "allogeneic" or "allograft" refers to transplantation of an organ from the same species of animal. In another embodiment, "allogeneic" transplants are preferred, with closest possible tissue typing (the greatest number of histocompatibility antigens in common between the donor and recipient) more preferred. In another embodiment, "xenogeneic" transplants, that is, transplantation of organs from other species of animal into a human, which, in one embodiment refers to transplantation with hearts from transgenic pigs, are also contemplated by the present invention.

In another embodiment, gene products associated with those identified herein are evaluated in the context of the methods of this invention, as predictors of transplant rejection. For example, CFLAR and BIRC1, genes associated with apoptosis would be evaluated in conjunction with other genes related to the apoptosis pathway, which in one embodiment, are also expected to be overexpressed, and if so, comprise additional embodiments of the invention.

In another embodiment, the present invention provides a method for identifying a candidate for successful allograft transplantation comprising determining a gene expression profile, wherein the expression profile comprises increased expression of at least 1 gene as compared with a standard, concurrent with diminished expression of at least 4 genes compared with said standard.

In one embodiment, the methods of the invention provide for the use of multiple assays, to evaluate differential gene expression. In another embodiment, arrays are used since microarray analysis allows in another embodiment simulataneous gene expression analysis of multiple genes in a high-throughput mode.

In one embodiment, the methods may be utilized to predict rejection or tolerance to a transplant. In one embodiment, gene profiling and the method for evaluating the same may comprise any embodiment listed herein for such purposes, and is part of this invention.

In one embodiment, the invention provides a kit for determining the likelihood of transplant rejection or in another embodiment, transplant tolerance. The kit of the invention provides in one embodiment a means for detecting the presence of a gene, indicative of transplant rejection in a biological sample from a subject, and in another embodiment, a means for determining whether the gene is present at an overexpressed level relative to the level present in a corresponding biological sample from a standard.

In one embodiment, the biological sample is cells, or in another embodiment tissue or in another embodiment peripheral blood. In one embodiment, the biological sample is obtained from a normal subject. The biological sample may, in one embodiment, be a tissue solution of a biopsy or in another embodiment, a sample of body fluid. In another embodiment, biological samples may refer to, blood, serum, plasma, tissue biopsy, organ biopsy, synovial fluid, urine, bile fluid, cerebrospinal fluid, saliva, mucosal secretion, effusion, or sweat The proteins of the sample may in one embodiment be distributed on various support matrices by methods specific to each matrix. Suitable matrices may, in one embodiment be paper, cellulose acetate, silica, glass, carbon, sugars, plastics and derivatives thereof, and a person skilled in the art will be familiar with the techniques of using such support matrices for the separation of proteins.

In another embodiment, the invention provides a kit for predicting transplant tolerance or rejection, comprising a microarray comprising immobilized nucleic acids, wherein said nucleic acids exhibit complementarity to a UQCRB, BTF3, ST13, CUL4A, TERF2IP, ARRB2, NPEPPS, ARRB2, NPEPPS, PIGB, APC, BCL7A, EDG4, IL17R, PGF, NFAT5, BIRC1, LILRB3, TM6SF2, CFLAR, SOD2, SLC16A3, and SCD4 gene, or fragments thereof.

In one embodiment, the kit comprises reagents for detecting the gene expression profile, wherein the reagents are nucleic acids, which may hybridize to mRNA isolated from a biological sample. In one embodiment, reagents may be labelled, or in another embodiment nucleic acids isolated from a biological sample are labelled. In another embodiment, the kit provides instructions for detecting the label qualitatively in another embodiment, quantitatively.

In another embodiment the kit further comprises a buffering agent, or in another embodiment, a preservative, or in another embodiment a protein stabilizing agent. In one embodiment, the kit further comprises an enzyme or a substrate. In one embodiment, the substrate may be a means of detecting a label, or in another embodiment the expressed protein product itself. In one embodiment, the kit further comprise reagents that are necessary for detection of nucleic acids, amino acids or hybridization signals for nucleic acids.

In one embodiment, detecting differential expression of the genes via the kits of the invention is accomplished using established PCR, ELISA, RIA, and other similarly recognized methods, and the reagents comprise those appropriate for the particular assay for detection.

In one embodiment, the results obtained are compared to a standard, which, in another embodiment, may comprise a series of standards, which, in another embodiment is used in the kits of the invention for quantification of differential expression. In one embodiment, the standard may comprise any embodiment listed herein, and in another embodiment, will be suitable for a particular application of the kit. In one embodiment, the standard comprises nucleic acids when the kit is used for the determination of nucleic acid profile, or in another embodiment the standard is a protein when the kit is used for the determination of expressed protein profile.

In one embodiment, the kit may be adapted for high-throughput screening, and comprise a microarray. In another embodiment, the array used is as described herein in Example 1.

In one embodiment, the kit further comprise agents, which in another embodiment may comprise antibodies, or other agents which detect activity or in another embodiment expression of the translated protein product. In one embodiment the agents comprise antibodies that detect the presence of specific nucleic acids.

In one embodiment, the kit comprises a microarray, which comprises cRNA of the genes indicated, and others. In one embodiment, the kit may comprise standard oligonucleotide probes, PCR reagents and detectable labels. In another embodiment, the kit may comprise biological samples taken from human subjects, which, in one embodiment may be blood or tissue, or in another embodiment cardiac tissue. The standard will comprise all embodiments listed herein for the standard, including in one embodiment nucleic acid from a specific tissue, or in another embodiment pooled samples as described herein.

In one embodiment, the present invention provide a kit that useful in predicting rejection or tolerance of tissue transplantation. In one embodiment, the values obtained by the kit of the invention are use for determining the probability of rejection versus tolerance. In another embodiment deviation from rejection may signal tolerance.

In one embodiment the kits of the invention evaluate multiple genes, and in another embodiment help in the generation of a gene expression profile, which is useful in the methods of this invention.

In one embodiment, the kit further comprises a positive and negative control, wherein said standards can be assayed and compared to the test sample. It is to be understood that the kits of the invention may be marketed for particular organ applications, such that the positive control is in one embodiment, a sample derived from a subject which rejected a cardiac allograft, and is to be used in determining cardiac transplant rejection.

Figure 5:
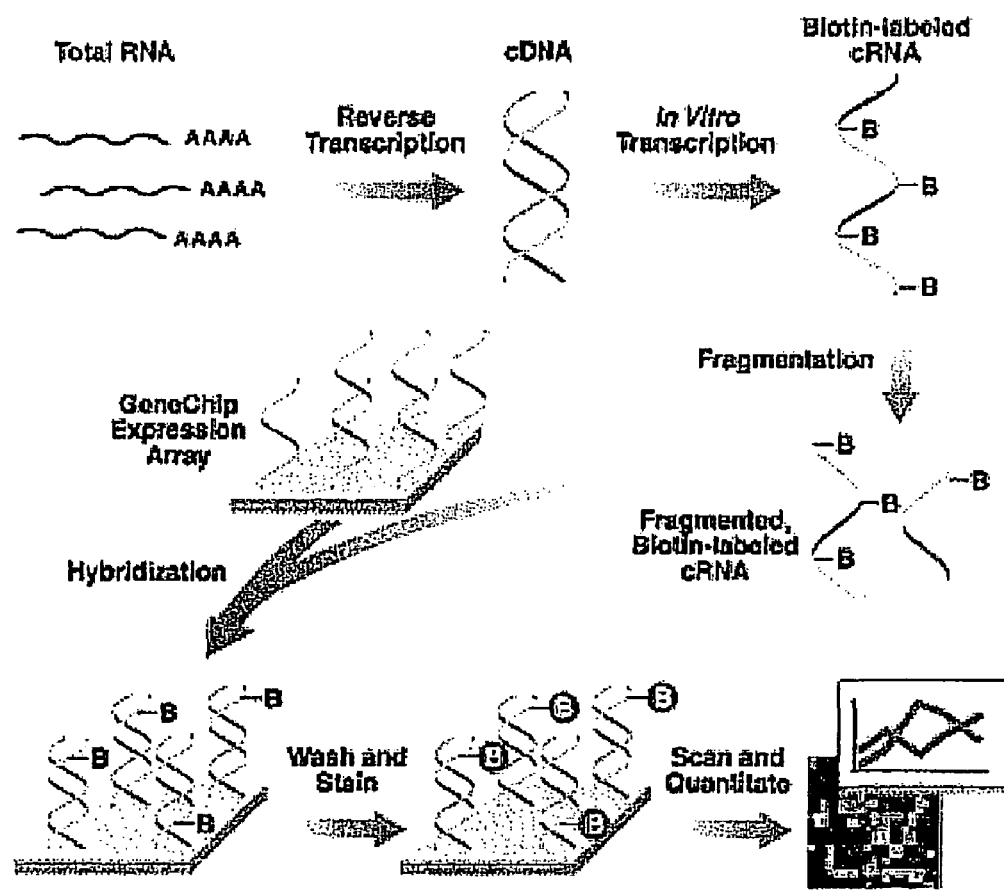
FIG. 5 is a graph showing Oligonucleotide microarrays method of assessing changes in gene expression levels using sample RNA transcripts.

In one embodiment, the kit may further comprise labeled cDNA. Fluorescently labeled cDNA probes may be generated through incorporation of fluorescent nucleotides by reverse transcription of RNA extracted from tissues of interest. Labeled cDNA probes applied to the chip, hybridize with specificity to each spot of DNA on the array. After stringent washing to remove non-specifically bound probes, (see FIG. 5) the chip is scanned by confocal laser microscopy. Quantification of hybridization of each arrayed element allows for assessment of corresponding mRNA abundance. With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression.

In one embodiment, the methods of this invention employ probes and primers, which may include repetitive stretches of adenine nucleotides (poly-A tails) normally attached at the ends of the RNA, for the identification of differentially expressed genes. In another embodiment, kits of this invention may comprise such probes.

In another embodiment, the invention provides a kit for predicting transplant tolerance or rejection, comprising a microarray comprising immobilized nucleic acids, wherein said nucleic acids exhibit complementarity to a UQCRB, BTF3, ST13, CUL4A, TERF2IP, ARRB2, NPEPPS, ARRB2, NPEPPS, PIGB, APC, BCL7A, EDG4, IL17R, PGF, NFAT5, BIRC1, LILRB3, TM6SF2, CFLAR, SOD2, SLC16A3, and SCD4 gene, or fragments thereof. In one embodiment, the microarray of the invention is exemplifies herein.

In one embodiment, the may comprise the expressed sequence tags of the invention, and in another embodiment, other expressed sequence tags, and the indicated genes.

A "microarray" refers in one embodiment to a spatially defined pattern of oligonucleotide probes on a solid support. "solid support" refers in one embodiment to a fixed organizational support matrix, such as silica, polymeric materials, or glass. In another embodiment, at least one surface of the substrate is partially planar. In one embodiment, it is desirable to physically separate regions of the substrate to delineate synthetic regions, such as, in one embodiment, with trenches, grooves, wells or the like. In another embodiment, solid substrates may refer to slides, beads and chips.

In one embodiment, the invention provides a medium having disposed thereon an oligonucleotide-hybridized cRNA of UQCRB, BTF3, ST13, CUL4A, TERF2IP, ARRB2, NPEPPS, ARRB2, NPEPPS, PIGB, APC, BCL7A, EDG4, IL17R, PGF, NFAT5, BIRC1, LILRB3, TM6SF2, CFLAR, SOD2, SLC16A3 or SCD4. In another embodiment, the medium may further comprise nucleic acid as described in Table IV. It is to be understood that a medium of this invention will incorporate the above-described sequences, and may further comprise additional oligonucleotides corresponding to sequences of the genome, whose function is as yet unknown, yet whose differential expression is correlated with transplant rejection or tolerance. In one embodiment, the medium further comprises cRNA of the expressed sequence tag as set forth in SEQ ID. Numbers 1 to 12. As would be appreciated by one skilled in the art, cRNA of the expressed sequence tags as set forth in SEQ ID. Nos. 1 to 12, could be generated by numerous known methods.

In one embodiment, cRNA refers to complementary ribonucleic acid or substantially complementary ribonucleic acid. In another embodiment, cRNA refers to the hybridization or base pairing between nucleotides or nucleic acids, such as, for instance, between the two strands RNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair in one embodiment, with at least about 70% of the nucleotides of the other strand, or in another embodiment with about 90% to 95%, and in another embodiment with about 98 to 100%.

The following examples are presented in order to more fully illustrate the preferred embodiments of the invention. They should in no way be construed, however, as limiting the broad scope of the invention.

EXAMPLES

Example 1

Correlating Cardiac Allograft Rejection and Peripheral Blood Gene Expression

Methods
Patient Population 409 blood samples were prospectively collected from 189 consecutive cardiac transplant patients referred for routine surveillance EMB.

Sample Collection

Blood obtained from a central venous sheath immediately prior to Endomyocardial Biopsy (EMB) was collected in RNA preservation solution (PAXgene™ Blood RNA Tubes, Qiagen Inc.) for immediate RNA stabilization and storage at −80° C. EMB specimens were processed and assessed by a cardiac pathologist and rejection grade was detenmed using the International Society for Heart and Lung Transplantation (ISHLT) grading system. This system categorizes biopsies into several grades (0, 1A, 1B, 2, 3A, 3B, and 4) based on the extent of lymphocyte infiltration, myocyte necrosis, and presence or absence of hemorrhage.

Study Design

A nested case-standard study of peripheral blood gene expression was performed within a cohort of biopsy patients. Samples isolated from subjects with the presence of rejection severe enough to mandate augmented immunosuppression according to clinical protocols (IHSLT grade 3A or higher) were referred to as "rejection" samples. Control patients samples ("Control") were isolated from subjects without clinically significant rejection (ISHLT grade 1A or lower). In order to minimize clinical confounders, both Rejection and Control samples were obtained from patients who had no clinical evidence of active infection or other acute illness at the time of biopsy, and whose recent clinical status had been stable at least one week prior to their scheduled biopsy. All case and control patients were treated with standard immunosuppression with corticosteroids, anti-metabolites, calcineurin inhibitors, and/or sirolimus.

In addition, blood specimens were obtained from the "rejection" subjects, following treatment with augmented immunosuppression, at a point in time where resolution of rejection was ascertained, i.e, when a grade of 2 or lower on repeat EMB was found. This group is referred to as "post-rejection" subjects, whose analysis provided for determining changes in a gene expression profile over time in the same patients during and after resolution of clinically significant rejection.

Microarray Sample Preparation and Hybridization

RNA samples from Control (n=7), Subjects classified in the rejection (n=7), and Post-Rejection (n=7) groups were purified using a commercial nucleic acid isolation column (PAXgene™ Blood RNA Column, Qiagen Inc.). Total RNA obtained from each sample was analyzed on an Agilent bioanalzyer and $OD_{260}/OD_{280}$ readings were taken. Individual cDNAs were prepared from each RNA isolate using reverse transcriptase (Superscript II primed by a poly (T) oligomer/T7 promoter, which was used as a template for producing biotin-labeled cRNA using an in vitro transcription reaction, resulting in a single cRNA for each blood sample. Each cRNA were hybridized to MAffynetrix HU133A oligonucleotide arrays, processed and scanned according to the manufacturer's instructions (see FIG. 5). All arrays (n=21) were hybridized on the same day by a single technician to avoid variability in hybridization conditions. Each array allows for the quantification of the expression of 22,215 transcripts (including full-length mRNA sequences and expressed sequence tags) derived from build 133 of the UniGene databases. Data were saved as raw image-files and converted into probe-set data (.cel files) using Microarray Suite (MAS 5.0, by Affymetrix).

Microarray Analysis

The analysis was carried out using robust multi-array analysis (RMA), since small data sets were analyzed. Software for RMA is available online for use in the R 1.70 package for statistical computing.

Differentially Expressed Genes in Rejection Compared to Control Samples

To determine candidate markers of rejection, three criteria were applied to the normalized data. First, data were filtered to include genes present above background on at least one array. Second, Significance Analysis of Microarrays (SAM) was used to correct for multiple comparisons and to select candidate markers of rejection using genes that were differentially expressed with an estimated overall false-discovery rate <0.10. Third, we required at least a 25% change in expression between Rejection and Control samples for a transcript to be of interest. The identities of differentially expressed genes were determined using annotation databases or via BLAST searches of the corresponding expressed sequence tags.

Response to Treatment

To determine whether candidate markers of rejection responded to immunosuppressive therapy, expression data was analyzed for these transcripts in patient samples, which were isolated from patients who had rejected the cardiac allografts. These samples were assessed in order to determine whether the expression pattern of the candidate genes paralleled what was seen in the subjects at baseline.

Expression of 91 candidate genes was differentially assessed for fold-changes in expression between control and samples isolated from subjects who rejected the allograft. Expression of the genes was also determined in samples isolated from the subjects post-rejection, and concordance between the expression patterns was determined. Fold changes greater than 1, whether increased or decreased expression, when found in two compared sample sets, with respect to a candidate gene, then such a gene is scored as concordant between the two samples.

The probability of selecting a set of 91 candidates by chance was estimated. 91 genes were randomly selected, a determination of gene concordance was made, with the total number of concordant genes in the randomly selected group computed. This process was repeated 10000 times, and a p-value was determined, reflecting the probability of a chance occurrence of the observed or better concordance.

Cluster Analysis

The capacity of candidate markers to distinguish Control, Rejection, and Post-Rejection samples was assessed using hierarchical clustering. Clusters were constructed using average linkage clustering and Pearson correlation coefficients as a measure of similarity using Cluster software and displayed using Treeview software.

Validation

Quantitative real-time polymerase chain reaction (qRT-PCR) was performed to validate changes in selected genes. Validation was performed with mRNA harvested from additional samples from the original biopsy cohort using the same selection criteria. RNA isolates were treated with DNAse to remove any contaminating genomic DNA and were subsequently converted to cDNA using an in vitro transcription reaction. cDNAs were used as templates for Taqinan qRT-PCR using ABI Assays-on-Demand on an ABI Prism 7900 sequence detection system. The specific assays used were Hs00153439_m1 (CFLAR), Hs00167309_m1 (SOD2), and Hs99999905_m1 (GAPDH). All samples were run in triplicate and GADPH was used as an internal control to normalize transcript abundance. Triplicates were averaged to calculate an expression value for each sample. Data were compared among Control, Rejection, and Post-Rejection samples using the Wilcoxon rank-smn test with $p<0.05$ indicating statistical significance.

Results

Patient Characteristics

As shown in FIG. 1, the frequency of rejection was low in the study population (FIG. 1). Of 409 EMB samples, 81% showed minimal or no evidence of allograft rejection (ISHLT grades 0, 1A or 1B) and 6% showed clinically significant rejection (grade 3A or higher). The characteristics of patients chosen for study are outlined in Table 1. All Control samples had Grade 0 rejection on biopsy and all Rejection samples were obtained from patients with rejection graded 3A or higher. The Post-Rejection samples were obtained a median of 55 days after rejection was first detected.

TABLE 1

Patient Characteristics

| | Control (n = 7) | Rejection (n = 7) | Post-Rejection* (n = 7) |
|---|---|---|---|
| Biopsy grade | | | |
| 0 | 7 | 0 | 3 |
| 1A | 0 | 0 | 2 |
| 1B | 0 | 0 | 2 |
| 2 | 0 | 0 | 0 |
| 3A | 0 | 5 | 0 |
| 3B | 0 | 2 | 0 |
| Age (years), median (range) | 61 (54-67) | 45 (28-66) | 45 (28-66) |
| Gender | | | |
| Female | 1 | 2 | 2 |
| Male | 6 | 5 | 5 |
| Type of immunosuppression† | | | |
| Double therapy | 2 | 1 | 0 |
| Triple therapy | 5 | 6 | 7 |
| Days post transplant, median (range) | 326 (8-1259) | 491 (7-1865) | — |
| Days of augmented immunosuppression, median (range) | — | — | 55 (14-76) |

*Rejection and Post-rejection represent the same patients during and after treatment of Grade 3A or higher rejection with augmented immunosuppression.
†Double therapy indicates (mycophenolate, azathioprine, or sirolimus) + (cyclosporine or tacrolimus); triple therapy indicates double therapy plus corticosteroids.

Microarray Analysis

Candidate Markers of Rejection

Of the 22,215 transcripts on each array, 10,826 (49%) were expressed at levels higher than background in at least one of the 21 samples evaluated. Of these, 91 gene products were differentially expressed in Rejection samples, as compared to Control (FIG. 2A, 2B, red) with a false discovery rate <0.10 after SAM analysis. FIGS. 2A and 2B graphically depict the differential gene expression in peripheral blood specimens from patients with biopsy-proven transplant rejection (n=7) and controls without rejection (n=7). As shown in red, 7 genes were over-expressed (FIG. 2A) and 84 genes were under-expressed in Rejection (FIG. 2B) samples. After treatment and resolution of rejection on follow-up endomyocardial biopsy, follow-up microarray analysis in these same patients (n=7) demonstrated that expression levels returned toward the level in control (blue; $p<0.0001$ by re-sampling). These genes were regarded as candidate markers for high-grade rejection. Overall good reproducibility in gene expression in these candidates is observed. The average coefficient of variation within each group (control or reject) was 4%. However, reproducibility was different for each gene, ranging from a minimum coefficient of variation of 1% to a maximum of 11%.

Changes in candidate markers was assessed after treatment of rejection by measuring expression levels in follow-up samples from the same patients. As shown in FIGS. 2A and 2B (blue), expression of nearly all of the candidate markers moved closer to a fold-change of one after immunosuppressive therapy, indicating a return toward levels in Control. This finding is consistent with the response to therapy noted on EMB. However, expression in the Post-Rejection samples did not fully normalize to a fold-change of one, suggesting that treated rejection has an intermediate expression profile between Control and Rejection. By randomly re-sampling gene expression data, we estimated the probability of finding a set of 91 genes that, by chance, showed differential expression in Rejection with concordant changes Post-Rejection.

Only 1 in 10,000 randomly selected sets of 91 genes showed this pattern (p=0.0001). Therefore, it is extremely unlikely that the observed intermediate expression profile occurred due to chance. These findings suggest that an expression profile that correlates with active rejection was identified in these patients.

Cluster Analysis

Hierarchical clustering was used as an additional method to characterize the ability of the candidate markers to distinguish Control, Rejection, and Post-Rejection samples. Hierarchical clustering referres in this case to a computational method that groups experimental samples according to similarity in patterns of gene expression across a large number of genes. 40 transcripts were selected, that showed at least a 25% change in expression between Control and Rejection and performed cluster analysis on this panel of genes. As shown in FIG. 3, samples cluster into two main branches with the primary hierarchical separation being the complete partitioning of Control and Rejection samples into separate branches.

FIG. 3 shows Cluster analysis of the 40 candidate markers analyzed with hierarchical clustering (see Table 2 for full names and functional annotation of the 40 candidates). Results are displayed using an Eisen plot, consisting of a dendrogram to demonstrate relationships among samples and a color-coded heatmap to display level of expression of individual genes. For each gene, red indicates higher than median expression and green indicates lower than median expression. As shown in the dendrogram, our candidate markers partition Rejection (R) and Control (C) samples into two main branches. Post-Rejection samples (p) are present in both main branches, indicating an intermediate expression profile for this group. Genes chosen for subsequent qRT-PCR validation are indicated with blue squares.

Post-rejection samples are present in both the Control and Rejection branches of the dendrogram, consistent with an intermediate expression profile for treated rejection.

Gene Function

The identities of the 40 candidate markers of rejection included 30 unique transcripts (Table 2). The majority of these are involved in the following cellular pathways: 1) transcription or translation, 2) cell-cycle regulation, 3) tumorgenesis/tumor suppression, 4) immune response, 5) apoptosis, and 6) intracellular signaling. Also included in the table are a number of expressed sequence tags (ESTs) of unknown function. Several transcripts are represented by multiple probe sets on the HU133A array. These replicate probe sets showed consistent changes during Rejection that resolved at Post-Rejection biopsy time-points (FIG. 3). The marker with the largest number of internal replicates was the gene CASP8 and FADD-like apoptosis regulator, an inhibitor of apoptosis that is down-regulated in rejection.

TABLE 2

Candidate Expression Markers of Cardiac Allograft Rejection

| Gene (Gene Symbol) | Protein Type/ Cellular Pathway | Fold-Change (Rejection versus Control) | Fold-Change (Post-Rejection versus Control) | Probe-Set ID* | UniGene ID[†] |
|---|---|---|---|---|---|
| ubiquinol-cytochrome c reductase binding protein (UQCRB) | Oxidative respiration | 2.25 | 1.3 | 205849_s_at | Hs.131255 |
| basic transcription factor 3 (BTF3) | RNA translation | 1.57 | 1.24 | 208517_x_at 211939_x_at | Hs.446567 |
| suppression of tumorigenicity 13 (ST13) | Tumor suppressor | 1.43 | 1.19 | 207040_s_at | Hs.377199 |
| cullin 4A (CUL4A) | Cell cycle/DNA replication | 1.34 | 1.1 | 201423_s_at | Hs.270788 |
| telomeric repeat binding factor 2, interacting protein (TERF2IP) | Transcription factor | 1.31 | 1.15 | 201174_s_at | Hs.274428 |
| arrestin, beta 2 (ARRB2) | Intracellular signaling | 0.75 | 0.79 | 203388_at | Hs.435811 |
| EST | | 0.75 | 0.99 | 207365_x_at | Hs.435123 |
| EST | | 0.74 | 0.96 | 207730_x_at | Hs.406701 |
| EST | | 0.74 | 0.86 | 205781_at | Hs.164410 |
| aminopeptidase puromycin sensitive (NPEPPS) | Proteinase | 0.73 | 0.91 | 201454_s_at | Hs.293007 |
| phosphatidylinositol glycan, class B (PIGB) | Cell surface protein | 0.73 | 0.8 | 205452_at | Hs.259326 |
| adenomatosis polyposis coli (APC) | Tumor suppressor | 0.72 | 0.9 | 216933_x_at | Hs.75081 |
| B-cell CLL/lymphoma 7A (BCL7A) | Cell cycle/DNA replication | 0.72 | 0.98 | 210679_x_at | Hs.371758 |
| endothelial differentiation, lysophosphatidic acid G-protein-coupled receptor, 4 (EDG4) | Cell cycle/DNA replication | 0.72 | 0.81 | 206722_s_at 206723_s_at | Hs.122575 |
| interleukin 17 receptor (IL17R) | Interleukin receptor | 0.72 | 0.79 | 205707_at | Hs.129751 |
| placental growth factor (PGF) | Hormone/ Angiogenesis Factor | 0.72 | 0.96 | 215179_x_at | Hs.252820 |
| EST | | 0.7 | 0.85 | 220712_at | Hs.493129 |
| EST | | 0.7 | 0.9 | 215558_at | Hs.485406 |
| EST | | 0.7 | 0.9 | 220071_x_at | Hs.14347 |
| nuclear factor of activated T-cells 5, tonicity-responsive (NFAT5) | Transcription factor | 0.7 | 0.83 | 208003_s_at | Hs.86998 |

TABLE 2-continued

Candidate Expression Markers of Cardiac Allograft Rejection

| Gene (Gene Symbol) | Protein Type/ Cellular Pathway | Fold-Change (Rejection versus Control) | Fold-Change (Post-Rejection versus Control) | Probe-Set ID* | UniGene ID† |
|---|---|---|---|---|---|
| EST | | 0.69 | 0.89 | 221205_at | |
| EST | | 0.69 | 0.89 | 215978_x_at | Hs.447720 |
| baculoviral IAP repeat-containing 1 (BIRC1) | Apoptosis | 0.68 | 0.76 | 204861_s_at | Hs.79019 |
| leukocyte immunoglobulin-like receptor, subfamily B, member 3 (LILRB3) | Leukocyte receptor | 0.68 | 0.81 | 210784_x_at 211135_x_at | Hs.306230 |
| EST | | 0.66 | 0.94 | 209703_x_at | Hs.288771 |
| transmembrane 6 superfamily member 2 (TM6SF2) | Cell surface protein | 0.66 | 0.88 | 210598_at | Hs.367829 |
| EST | | 0.65 | 0.9 | 215375_x_at | Hs.438377 |
| EST | | 0.65 | 0.94 | 215029_at | Hs.293563 |
| CASP8 and FADD-like apoptosis regulator (CFLAR) | Apoptosis | 0.59 | 0.73 | 211862_x_at 210564_x_at 208485_x_at 211317_s_at 214486_x_at | Hs.355724 |
| superoxide dismutase 2, mitochondrial (SOD2) | Oxidative stress | 0.56 | 0.83 | 221477_s_at | Hs.384944 |
| EST | | 0.55 | 0.84 | 216109_at | Hs.435249 |
| solute carrier family 16, member 3 (SLC16A3) | Membrane transport | 0.54 | 0.66 | 202856_s_at | Hs.386678 |
| stearoyl-CoA desaturase 4 (SCD4) | Fatty acid metabolism | 0.5 | 0.87 | 220232_at | Hs.379191 |

*Probe-Set ID: indicates the corresponding probe-set on the Affymetrix HU 133A microarray.
†Unigene ID information are available online at NCBI website.
EST indicates Expressed Sequence Tag Quantitative PCR Transcriptional changes were verified using qRT-PCR for two genes: CASP8 and FADD-like apoptosis regulator (CFLAR) and superoxide dismutase 2 (SOD2). Consistent with the microarray analysis, both genes were significantly down-regulated during rejection, with a mean fold-change of 0.76±0.06 (p=0.01) for CFLAR and a mean fold-change of 0.74±0.09 (p=0.02) for SOD2, as shown in FIG. 4.

Figure 4:
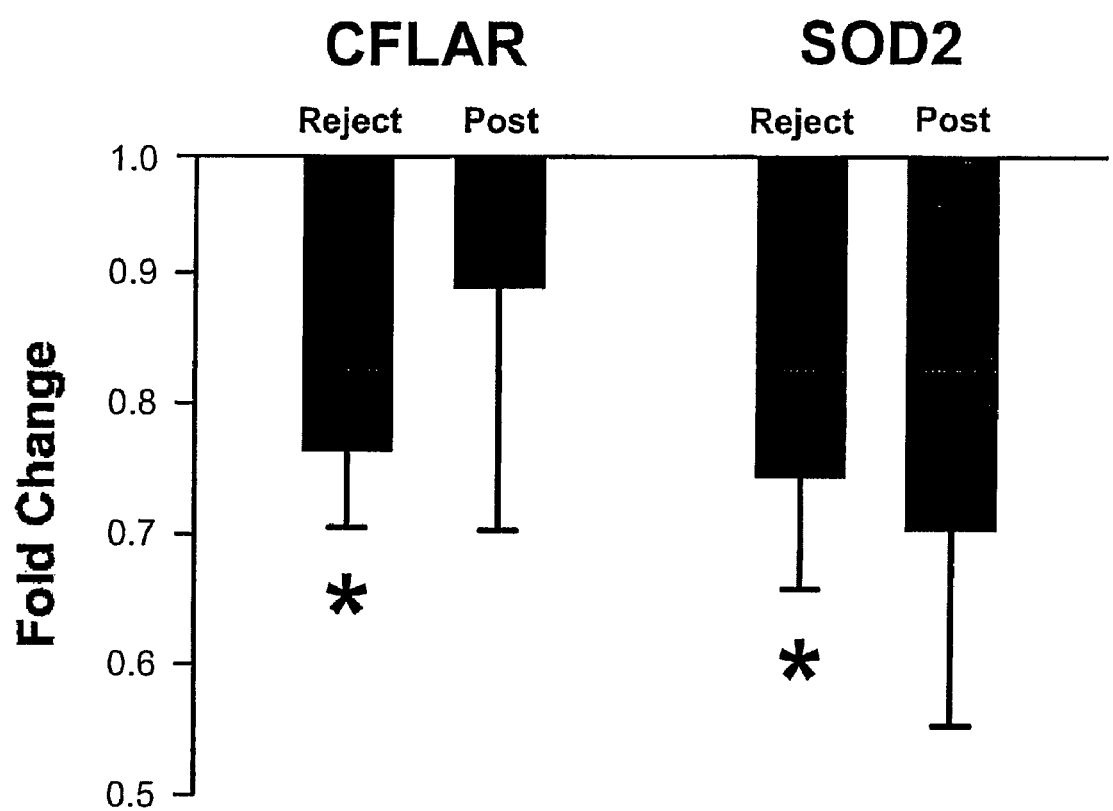
FIG. 4 is a graph of showing the quantified transcript abundance of two candidate markers, CFLAR and SOD2, using qRT-PCR. Data are displayed as fold-changes in expression in Rejection (n=10) and Post-Rejection (n=8) samples, each compared to a Standard (n=5).

FIG. 4 graphically depict the transcriptional changes verified using qRT-PCR. Data are displayed as fold-changes in expression in Rejection (n=10) and Post-Rejection (n=8) each compared to Control (n=5). In agreement with the microarray findings, both CFLAR and SOD2 expression were decreased in Rejection. CFLAR expression returned toward Control levels in Post-Rejection samples, and SOD2 expression remained low, consistent with persistent partial activation of circulating leukocytes after treatment of rejection. *p<0.05 compared to Control by Wilcoxon rank-sum test.

Thus, peripheral blood gene expression changes observed by microarray profiling were confirmed in comparisons of Rejection and Control samples. In Post-Rejection samples, CFLAR expression trended back toward Control levels, with a fold-change closer to 1.0, but SOD2 did not. The partial return towards baseline for CFLAR and the lack of return for SOD2 likely reflect persistent partial activation of circulating leukocytes in these samples, which were taken at variable times after histologic resolution of rejection.

Figure 6:
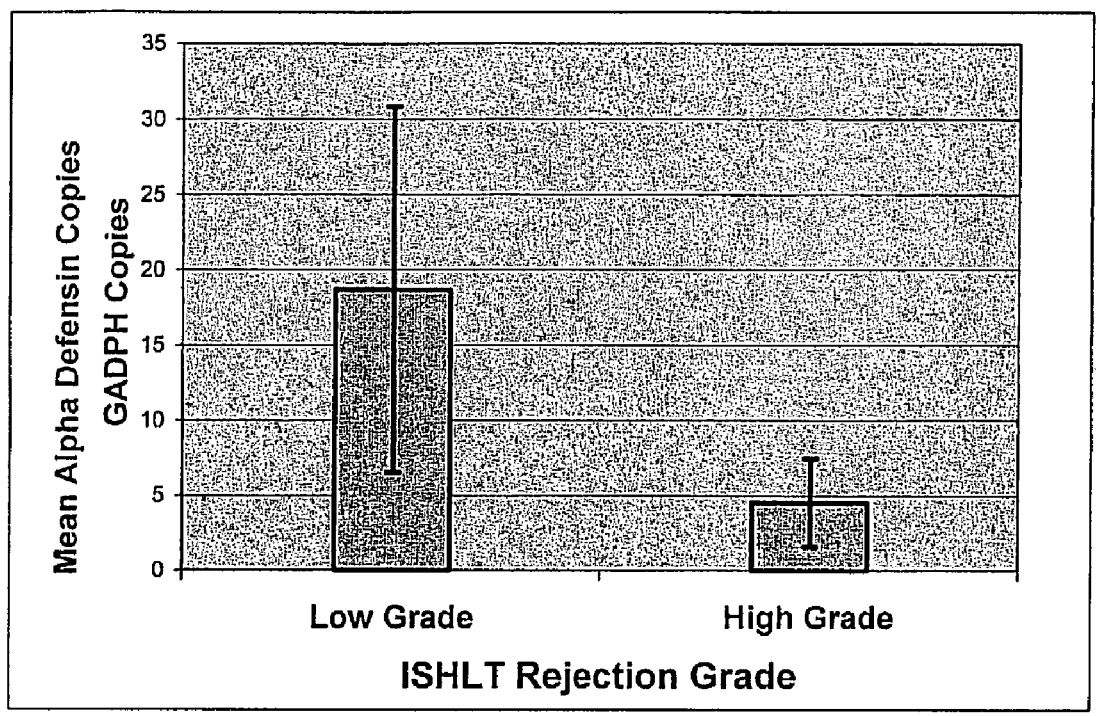
FIG. 6 is a graph showing quantitative PCR detection of peripheral blood expression of α-1 Defensin.

FIG. 6. shows quantitative PCR on 24 samples. The Y axis shows the normalized alpha defensin MRNA levels. The x-axis, shows the samples divided into those drawn during an episode of high grade rejection, ISHLT grade 2 or higher or during an episode of low grade rejection In these additional samples, there appears to be a trend toward higher mean defensin expression levels in the samples from patients at the time of low grade rejection as compared to those at the time of high grade. This trend in Alpha-1-defensin expression correlates with the pattern seen in the initial microarray findings.

Discussion

Peripheral blood gene expression correlated herein with cardiac allograft rejection. 40 transcripts were identified, that were altered in acute cellular rejection and returned toward normal in response to augmented immunosuppression. Moreover, in two separate analyses, treated rejection had an intermediate expression profile, suggesting persistent immune activation despite resolution of rejection on biopsy. These findings raise the possibility that expression profiling may prove to be a more sensitive screening test for rejection than EMB.

As shown in Table 2, the known or proposed function of the candidate markers involve cellular processes that are plausible components of an immune response, such as regulation of DNA transcription or translation, cell cycle and apoptosis regulators, and markers of immune system activation. It is possible that changes in expression of genes involved in the regulation of programmed cell death, such as CFLAR, promote clonal expansion of specific lymphocyte populations as part of the rejection process.

Expression profiling is therefore a powerful technique, but it creates substantial challenges resulting from the analysis of many genes in a small number of samples. These concerns were addressed at multiple levels. First, conservative normalization and gene selection strategies that are superior in the analysis of relatively small data sets was used. Second, serial measurements in the same patients, which reduced the impact of inter-patient variability were incorporated. Third, selected findings using quantitative PCR were validated. Fourth, analyses were performed on immediately preserved wholeblood isolates, minimizing the impact of sample pre-processing procedures, such as cell-sorting or buffy coat isolation, on the gene expression profile and is more convenient to implement in a clinical setting.

This invention demonstrates that peripheral gene expression correlates with cardiac allograft rejection detected on EMB. 40 transcripts were identified that are altered in acute cellular rejection and returned toward normal in response to augmented immunosuppression. Moreover, treated rejection has an intermediate expression profile, which suggests persistent immune activation despite resolution of rejection on biopsy. These findings prove the possibility that expression profiling may be a more sensitive screening test for rejection than EMB. In conclusion, the principle that peripheral blood gene expression correlates with cardiac allograft rejection has been demonstrated.

While various embodiments of the present invention have been described above, it should be understood that they have been presented by way of example only, and not limitation. Thus the breadth and scope of the present invention should not be limited by any of the above described exemplary embodiments, but should be defined only in accordance with the following claims and their equivalents.

What is claimed is:

1. A method for identifying cardiac transplant tissue rejection in a human subject, said method comprising:

determining a first gene expression profile in a blood sample taken from said human subject, wherein said first gene expression profile comprises the nucleic acid expression level of the ubiquinol-cytochrome c reductase binding protein (UQCRB) gene; and comparing said first gene expression profile to a second gene expression profile, wherein said second gene expression profile comprises the nucleic acid expression level of the UQCRB gene derived from blood samples collected from a human cardiac transplant population that does not have cardiac transplant tissue rejection, wherein a statistically significant increase in UQCRB gene expression in said first gene expression profile compared to said second gene expression profile is indicative of cardiac transplant tissue rejection in said human subject.

2. The method of claim 1, wherein said first and second gene expression profiles further comprise the nucleic acid expression level of the basic transcription factor 3 (BTF3) gene, the suppression of tumorigenicity 13 (ST13) gene, and the cullin 4A (CUL4A) gene.

3. The method of claim 2, wherein a statistically significant increase in BTF3, ST13, or CUL4 gene expression in said first gene expression profile compared to said second gene expression profile is indicative of cardiac transplant tissue rejection in said human subject.

4. The method of claim 1, wherein said first and second gene expression profiles further comprise the nucleic acid expression level of the CASP8 and FADD-like apoptosis regulator (CFLAR) gene.

5. The method of claim 4, wherein a statistically significant decrease in CFLAR gene expression in said first gene expression profile compared to said second gene expression profile is indicative of cardiac transplant tissue rejection in said human subject.

6. The method of claim 1, wherein said first and second gene expression profiles comprise the nucleic acid expression level of a plurality of expressed sequence tags (ESTs).

7. The method of claim 6, wherein at least one of said expressed sequence tags comprises a nucleic acid comprising SEQ ID NO: 12.

8. The method of claim 1, wherein the identified caridac transplant tissue rejection is a cardiac allograft.

9. The method of claim 1, wherein said determining a first gene expression profile is conducted by the use of a microarray.

* * * * *